United States Patent
Wessel

(10) Patent No.: US 6,699,188 B2
(45) Date of Patent: *Mar. 2, 2004

(54) INTERACTIVE REWARD DEVICES AND METHODS

(75) Inventor: Paul Wessel, Delano, MN (US)

(73) Assignee: Guidance Interactive Technologies, Delano, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 10/116,696

(22) Filed: Apr. 3, 2002

(65) Prior Publication Data

US 2003/0050537 A1 Mar. 13, 2003

Related U.S. Application Data

(63) Continuation-in-part of application No. 09/884,968, filed on Jun. 21, 2001, now Pat. No. 6,494,830.
(60) Provisional application No. 60/213,422, filed on Jun. 22, 2000.

(51) Int. Cl.[7] .................................................. A61B 5/00
(52) U.S. Cl. ........................ 600/300; 128/920; 434/235
(58) Field of Search ................................. 600/300–301, 600/309–310, 316, 322, 347, 365, 481, 500, 587, 595; 128/903–904; 702/19, 104; 379/106.1, 106.2; 434/235–238, 262; 273/429, 440, 459, 148 B

(56) References Cited

U.S. PATENT DOCUMENTS

| | | |
|---|---|---|
| 5,134,391 A | 7/1992 | Okada |
| 5,307,263 A | 4/1994 | Brown |
| 5,483,276 A | 1/1996 | Brooks et al. |
| 5,542,420 A | 8/1996 | Goldman et al. |
| 5,549,117 A | 8/1996 | Tacklind et al. |
| 5,551,953 A | 9/1996 | Lattin et al. |
| 5,572,421 A | 11/1996 | Altman et al. |
| 5,596,994 A | 1/1997 | Bro |
| 5,601,435 A | 2/1997 | Quy |
| 5,673,692 A * | 10/1997 | Schulze et al. ............. 600/300 |
| 5,678,571 A | 10/1997 | Brown |
| 5,730,654 A | 3/1998 | Brown |
| 5,827,179 A | 10/1998 | Lichter et al. |
| 5,832,448 A | 11/1998 | Brown |
| 5,840,020 A | 11/1998 | Heinonen et al. |
| 5,857,967 A | 1/1999 | Frid et al. |
| 5,876,351 A | 3/1999 | Rohde |
| 5,899,855 A | 5/1999 | Brown |
| 5,913,310 A | 6/1999 | Brown |
| 5,918,603 A | 7/1999 | Brown |
| 5,933,136 A | 8/1999 | Brown |

(List continued on next page.)

OTHER PUBLICATIONS

Busch, Fritz, "Diabetes Institute Brings Dakota, New Ulm Together," New Ulm Journal, Jun. 10, 2001, <www.oweb.com/newulm/journal/stories/n061001.html>.

Newsgroup Posting, "Idea Only for radical new bG meter," Newsgroup misc.health.diabetes, Jun. 20, 1995.

*Primary Examiner*—Michael Astorino
(74) *Attorney, Agent, or Firm*—Dicke, Billig & Czaja, PLLC

(57) ABSTRACT

A patient is rewarded for performing a medical test or for maintaining medical test results within desired levels. Medical test data is generated and transferred for use by reward firmware in a cartridge, for example. Reward information is provided to the patient to motivate or encourage the patient to conduct medical tests and/or to maintain medical test results within certain levels. The cartridge can be inserted into an electronic controller, e.g. a handheld video-game controller, cellular telephone, or other device. Transmission of data and/or encouragement to and from a remote location provides additional advantages.

20 Claims, 25 Drawing Sheets

U.S. PATENT DOCUMENTS

| | | |
|---|---|---|
| 5,940,801 A | 8/1999 | Brown |
| 5,950,632 A | 9/1999 | Reber et al. |
| 5,951,300 A | 9/1999 | Brown |
| 5,960,403 A | 9/1999 | Brown |
| 5,961,451 A * | 10/1999 | Reber et al. ............... 600/322 |
| 5,983,120 A | 11/1999 | Groner et al. |
| 6,024,699 A | 2/2000 | Surwit et al. |
| 6,047,259 A | 4/2000 | Campbell et al. |
| 6,083,104 A | 7/2000 | Choi |
| 6,101,478 A | 8/2000 | Brown |
| 6,102,846 A | 8/2000 | Patton et al. |
| 6,159,147 A | 12/2000 | Lichter et al. |
| 6,167,362 A | 12/2000 | Brown et al. |
| 6,168,563 B1 | 1/2001 | Brown |
| 6,210,272 B1 | 4/2001 | Brown |
| 6,249,809 B1 * | 6/2001 | Bro ............................. 709/217 |
| 6,295,506 B1 * | 9/2001 | Heinonen et al. ............ 702/104 |
| 6,379,301 B1 * | 4/2002 | Worthington et al. ........ 600/309 |
| 6,440,068 B1 * | 8/2002 | Brown et al. ................. 600/300 |
| 6,443,890 B1 * | 9/2002 | Schulze et al. ............. 600/300 |
| 6,478,736 B1 * | 11/2002 | Mault ........................ 600/300 |
| 6,513,532 B2 * | 2/2003 | Mault et al. ................. 128/921 |
| 6,571,200 B1 * | 5/2003 | Mault ......................... 702/182 |

* cited by examiner

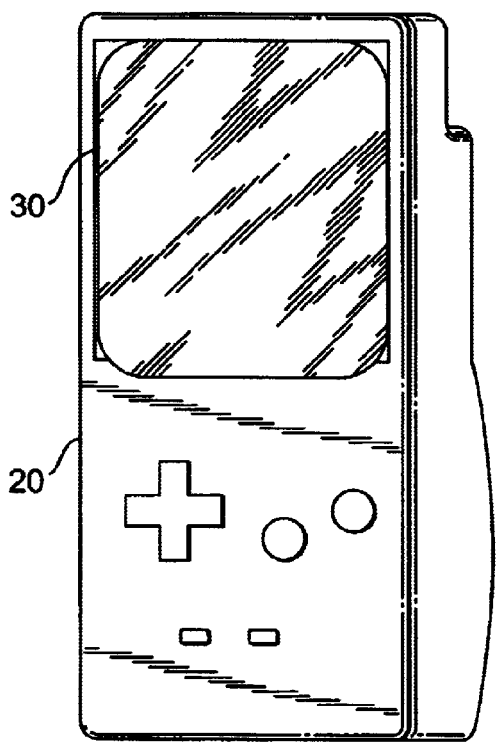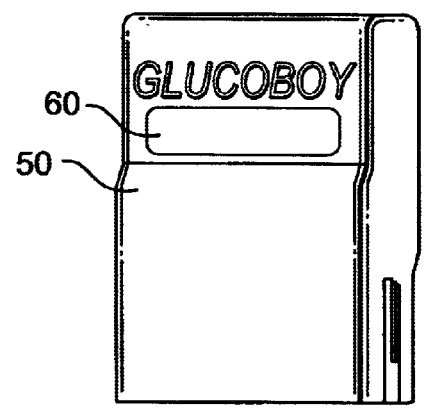
Fig. 6
Fig. 7

INTERACTIVE REWARD DEVICES AND METHODS

CROSS-REFERENCE TO RELATED APPLICATIONS

This application is a Continuation-In-Part of U.S. patent application Ser. No. 09/884,968 now U.S. Pat. No. 6,494,830B1, filed Jun. 21, 2001, priority to which is claimed under 35 U.S.C. §120 and which is incorporated herein by reference. Further, parent U.S. Pat. No. 6,494,830B1 claims priority under 35 U.S.C. §119(e) to U.S. Provisional Patent Application No. 60/213,422, filed Jun. 22, 2000, which is incorporated herein by reference.

BACKGROUND OF THE INVENTION

Juvenile diabetes strikes about 15,000 children every year under the age of 20. Currently, the United States has over 200,000 of these children that daily struggle with this disease. Contraction of diabetes requires the afflicted to frequently monitor blood glucose in order to avert long-term damage to their kidneys, eyes, and feet. However, there are no known blood glucose testing devices currently available that provide or incorporate any motivation or reward mechanisms to encourage the individual to continue this testing regimen. Because the majority of the diabetic population is adults, most commercially available glucose testing meters are designed in such a fashion that is not user-friendly or socially acceptable to children. This causes children to shy away from blood glucose testing in a social setting. This anti-social aspect could endanger them to episodes of hypoglycemia, hyperglycemia, and or insulin shock, among other short-term and long-term problems.

Abstinence from regular blood glucose testing, for any reason, can have a devastating impact on the long-term wellness of the diabetic adolescent and contribute to significant increases in future health care costs. There have been many articles written and scientific studies conducted about incorporating motivational stimuli into medical testing procedures. Many positive outcomes have been realized and the increased testing compliance has been achieved. See, for example, Lieberman, Debra, "Health Education Video Games for Children and Adolescents: Theory, Design, and Research Findings", paper presented at the annual meeting of the International Communications Association, Jerusalem, 1998, which is incorporated herein by reference.

Researchers in the field of diabetes are exploring technologies and methodologies to perform non-invasive glucose blood-level monitoring in type I and II diabetics. Currently, there are two popular types of technology used in determining blood glucose levels that are found in the majority of home glucose monitoring devices. The first is the colormetric type, and the second is an enzyme/current differential device. The colormetric method requires placement of a small blood sample on a chemically treated test strip. The amount of glucose in the blood changes the color of the chemically treated test strip. A differential measurement is then taken from the test strip without a blood sample and compared to the color of the test strip once the blood has been placed on the strip and a finite testing period has been allowed to elapse. The enzyme/current differential method determines proper blood glucose by determining the amount of current change that takes place when a glucose blood sample is placed on the test strip, using e.g. biosensor technology. An enzyme coating of the test strip directly affects the electrical resistance of the test strip. With both technologies, proper glucose level is determined by comparison of either the color properties or the electrical current change in the test strip.

One of the most difficult challenges in the glucose testing device market has been to develop a glucose-testing device that does not require a small capillary blood sample. The "non-invasive" approach would become a huge commercial success because it would eliminate the element of pain associated with extracting a blood sample and increase the frequency of blood glucose testing.

It is public knowledge that one of the non-invasive approaches that could become commercially available is using a series of EKG/EEG readings, associated with a host of complex algorithms to determine blood glucose levels. It is not believed, however, that there are not any commercially available products incorporating such technologies and/or methodologies, although a commercially viable EKG/EEG glucose-monitoring device may soon become available. It is also believed that due to this research, other new products, incorporating other sensors, might become available to detect epileptic seizures and asthma attacks.

SUMMARY OF THE INVENTION

A glucose meter according to an embodiment of the invention includes an input device adapted to receive physiological input from a patient. A processor is operatively coupled with the input device, the processor being adapted to produce a blood glucose value based on physiological input received by the input device. The processor is also adapted to generate an electrical signal related to blood glucose value. An output device is operatively coupled with the processor, the output device being adapted to communicate the blood glucose value directly to a user of the glucose meter. A connector is used for connecting the glucose meter to an electronic controller distinct from the glucose meter, the connector being adapted for communicating to the electronic controller an electrical signal generated by the processor. A modular housing supports at least the processor and the output device and is for insertion into or other physical connection with the electronic controller, such that the connector automatically can align with, and connect to, the electronic controller for communication of the connector electrical signal to the electronic controller to motivate or reward the patient.

According to an alternative aspect of the invention, an apparatus for encouraging compliance with medical monitoring or treatment includes medical circuitry for generating one or more medical monitoring or treatment parameters, a power supply for powering the medical circuitry, and motivation circuitry for rewarding and/or motivating a patient, the motivation circuitry being operatively coupled with the medical circuitry and being adapted for communication with an external device for communicating reward and/or motivational information to a user of the apparatus based on the medical monitoring or treatment parameters. The motivation circuitry is powered by the external device and not by the power supply for powering the medical circuitry.

According to an alternative aspect of the invention, a handheld video-game system for use by a patient includes a video-game controller for receiving game cartridges, the video-game controller comprising a first display for entertaining the patient, and a medical diagnostic cartridge constructed for receipt by the video-game controller, the medical diagnostic cartridge comprising a second display, separate from the first display, for displaying medical information to the patient. The controller is adapted to receive medical data from the medical diagnostic cartridge and to display additional information based on the medical data to the patient on the first display.

According to an alternative aspect of the invention, a method of rewarding a patient for a medical test includes generating medical test data based on a medical test, transferring the medical test data for use by reward firmware, and providing reward information to the patient, the reward information being for rewarding the patient for conducting the medical test or for rewarding the patient for maintaining results of the medical test within specified parameters, as represented in the medical test data. According to an alternative aspect of the invention, a medical testing and reward apparatus includes a medical testing device, a reward-based incentive device operably coupled with the medical testing device, and means for correlating (1) how well a patient follows a testing regimen or achieves a certain medical test result using the medical test device with (2) a reward level provided to the patient by the reward-based incentive device.

According to an alternative aspect of the invention, a glucose monitoring apparatus includes a glucose-monitoring device adapted to receive a blood sample, the glucose-monitoring device being in the form of a cartridge and adapted to accommodate insertion of a blood glucose test strip directly into the cartridge for generation of glucose values. Interactive and motivational software are incorporated into the cartridge. The apparatus includes a storing device for storing the glucose values, a hand-held controller for receiving the cartridge, the hand-held controller using the stored values and the interactive and motivational software to interact with and motivate a user of the apparatus. A transmission device is operably coupled with the hand-held controller to transmit the stored values to a remote location, according to one aspect.

According to another aspect of the invention, a method of medical data transmission includes using a medical monitoring device in the form of a cartridge to generate medical data, connecting the cartridge to a cellular telephone, transmitting the medical data by a pre-existing cellular telephone network to a remote location, and transmitting a message from the remote location to the cellular telephone to provide direct feedback regarding the medical data. According to aspects of the invention, the medical data is blood glucose data and the medical monitoring device is a blood-glucose monitoring device.

These and other aspects of the invention will be evident to those of ordinary skill upon reading this disclosure.

BRIEF DESCRIPTION OF THE DRAWINGS

Embodiments of the invention will be described with reference to the figures, in which like reference numerals denote like elements and in which:

FIG. 6 is a front view of a controller, according to an embodiment of the invention;

FIG. 7 is a front view of a cartridge, according to an embodiment of the invention;

DETAILED DESCRIPTION OF PREFERRED EMBODIMENTS

Figure 1:
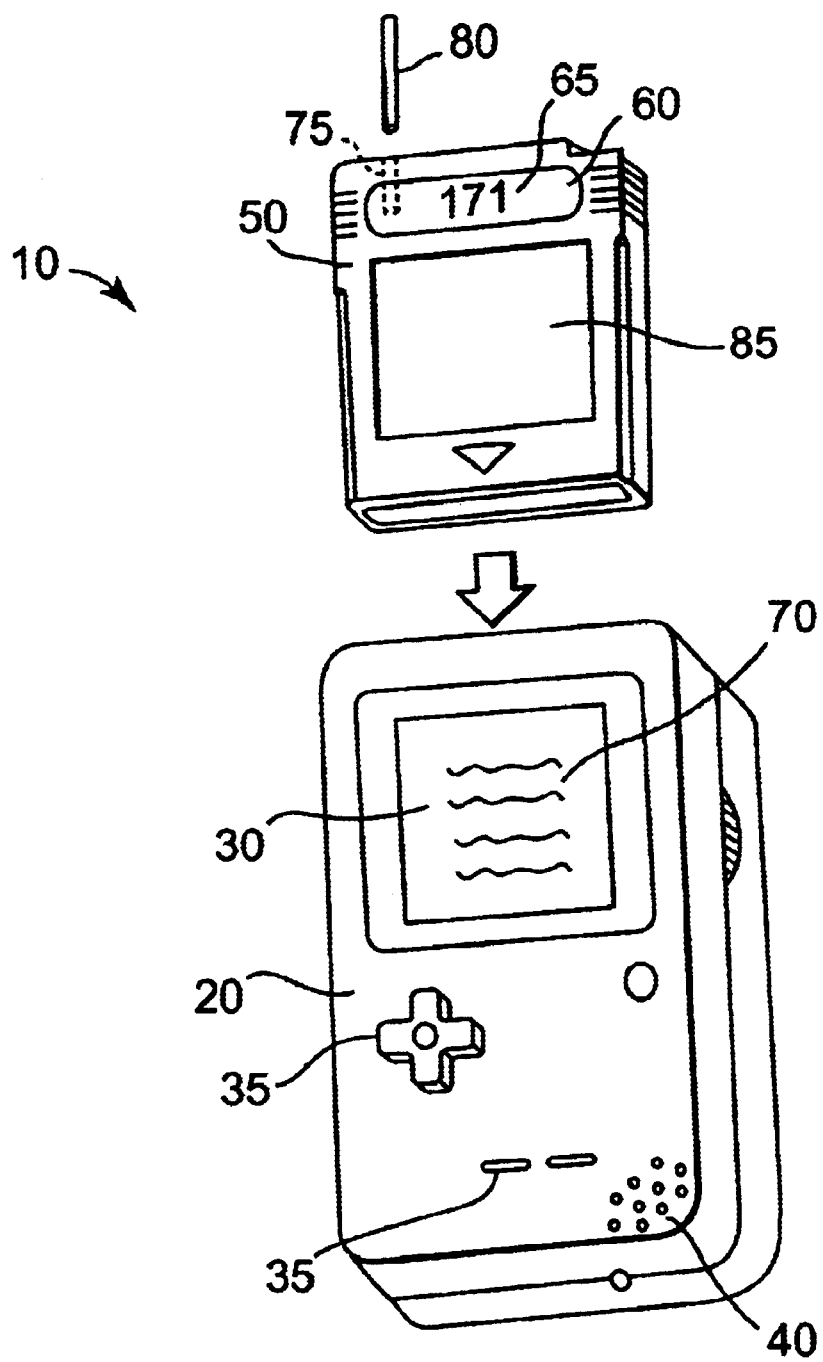
FIG. 1 is a perspective view of a cartridge and controller according to an embodiment of the invention.

Particular embodiments of the invention will be described with respect to blood glucose meters or blood-glucose measuring devices for use in managing and controlling e.g. Type I diabetes. Additionally, particular embodiments of the invention will be described with respect to video-game controllers, such as the GAME BOY video-game controller available from Nintendo. However, embodiments of the invention extend to other medical tests or procedures, beyond just glucose testing, and to other controllers, such as cellular telephones, personal digital assistants, and other computing devices, to name a few examples. Therefore, although aspects of the invention may be described with respect to video game controllers and glucose monitoring as specific examples, the invention should not be considered limited to those examples.

Embodiments of the invention now will be described with more specific reference to the figures. According to one aspect of the invention illustrated in FIG. 1, handheld video game system 10 for use by a patient includes video-game controller 20 for receiving game cartridges. Video-game controller 20 includes first display 30 for entertaining or otherwise informing the patient, for example by displaying video-game graphics, charts, tables, or other information. Controller 20 also includes control buttons, keys, or similar manually activated devices 35, speaker 40, and other interactive features found e.g. on a conventional GAME BOY handheld gaming controller. Other types of controllers contemplated according to embodiments of the invention include PALM PILOT devices, personal digital assistants, cellular telephones, and/or other off-the-shelf computing devices.

System 10 also includes medical cartridge 50, for example a medical diagnostic cartridge, constructed for receipt by controller 20. Cartridge 50 can be inserted into or otherwise physically connected to the same cartridge slot, interface or other connection device used by controller 20 to receive commercial software gaming cartridges, for example. One such insertion point is located on the top or back of controller 20, but other insertion points or interfaces, in different locations on or in controller 20, are contemplated and will be apparent to those of ordinary skill upon reading this disclosure.

According to one embodiment, cartridge 50 includes display 60, which is a second display of system 10 separate from first display 30, for displaying medical information 65 to the patient. Such medical information can include a blood glucose reading, for example. Controller 20 is adapted to receive medical data from medical cartridge 50 and to display additional information 70, based on or using the medical data, to the patient on first display 30. As shown in FIG. 1, first display 30 and second display 60 are disposed to face the same direction when cartridge 50 is received by controller 20. Of course, other directional dispositions are contemplated. According to embodiments of the invention, one or both of displays 30, 60 are LED or LCD or other types of visual display panels powered by an appropriate power supply and driven by associated circuitry, as will be described.

According to embodiments of the invention, cartridge 50 is a glucose meter, for example a stand-alone glucose meter that functions as such entirely by itself without need for connection to controller 20 or any other external device. Because cartridge 50 thus does not rely on display 30 or any other feature of controller 20 for interpreting or displaying medical information, controller 20 is not necessarily subject to e.g. U.S. Food and Drug Administration approval or other regulatory approval as a medical device, for example under the Section 510(k) premarket notification provisions for in vitro medical devices. According to aspects of the invention, display 30 of controller 20 is used only to display e.g. reward codes, games, prizes, and other non-medical incentives that should not subject controller 20 to such approval.

According to one embodiment, cartridge 50 is a glucose meter comprising an input device adapted to receive physiological input from a patient. The input device can take various forms, e.g. slot 75 defined in cartridge 50 to accommodate insertion of blood glucose test strip 80. Although slot 75 is illustrated as having a vertical orientation with placement at roughly the upper left corner of cartridge 50, it is of course possible for slot 75 to be located at one or more other portions of cartridge 50, e.g. on any of the sides or either the front or back face of cartridge 50. Other input devices are contemplated according to embodiments of the invention. For example, a blood receptor, blood receiving area, other receptor, or the like can be disposed e.g. on face 85 of cartridge 50, as can an optical or other non-invasive sensing or input device for determining blood glucose readings or other medical parameters.

Figure 2:
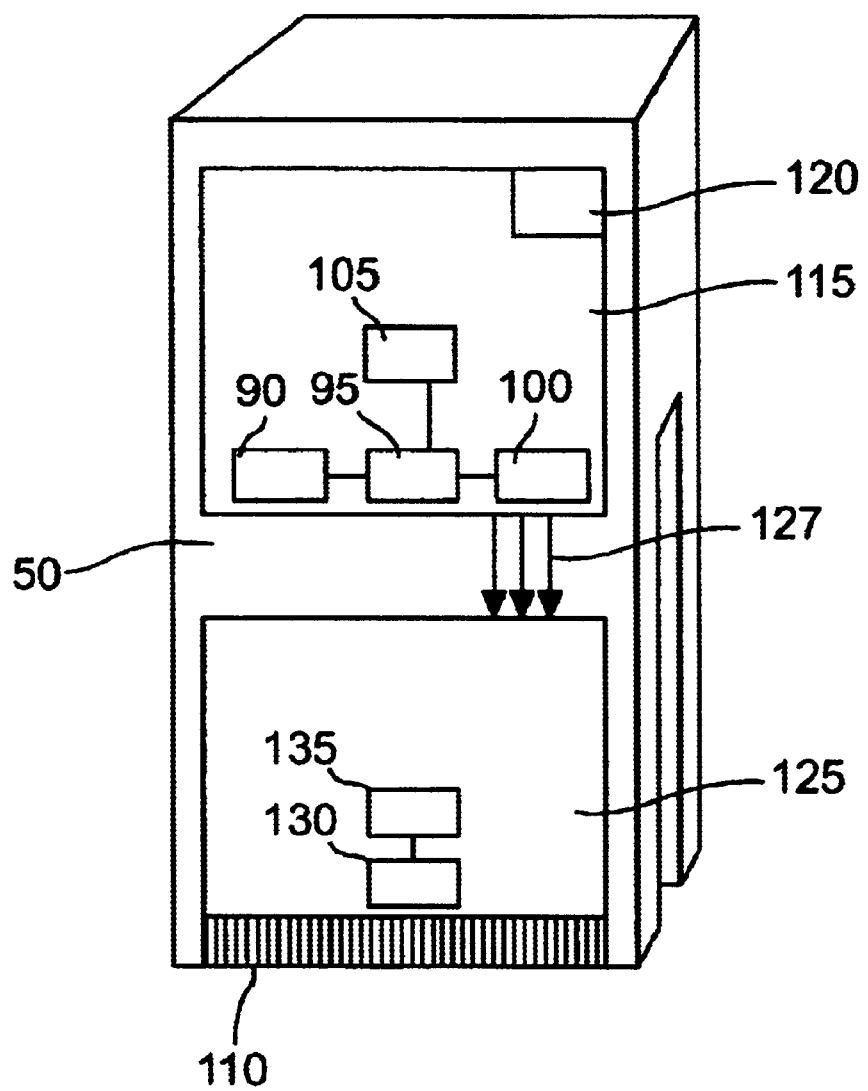
FIG. 2 is a generally schematic view of a cartridge according to an embodiment of the invention.

FIG. 2 is a schematic view of cartridge 50 according to embodiments of the invention. Input device circuitry 90 is connected to the input device adapted to receive physiological input from the patient, whether the input device is in the form of slot 75, other device on face 85, or any of the other input devices described herein. Processor 95 is operatively coupled with the input device and the input device circuitry, the processor being adapted to produce a blood glucose value or indication based on the physiological input received by the input device. Processor 95 is also adapted to generate an electrical signal related to the blood glucose indication.

Processor 95 is operatively coupled with output device circuitry 100, which itself is operatively coupled with e.g. output device 60 in the form of a display. Output device 60 is adapted to communicate blood glucose indication 65 or other information directly to a user of glucose meter cartridge 50. Those of ordinary skill in the art will appreciate that input device circuitry 90 and output device circuitry 100 can be directly connected to and/or formed as a part of or unitarily with their respective input and output devices. Processor 95 is also operatively coupled with memory or storing device 105 for storing glucose values or other medical diagnostic or medically related data.

Cartridge 50 also includes connector 110 constructed to connect glucose meter cartridge 50 to electronic controller 20. Controller 20 is distinct from glucose meter cartridge 50. Connector 110 is adapted to communicate to electronic controller 20 an electrical signal related to the electrical signal generated by processor 95. According to embodiments of the invention, the signal communicated to controller 20 is not directly discernible as or representative of a blood glucose reading itself, but instead is a reward-related or motivation-related signal. In this way, controller 20 is more likely free of government medical-device regulatory requirements, referenced above, and the patient or other user is unable, or at least less likely, to use controller 20 as a direct and/or sole blood glucose management tool in the manner of a medical device.

As will be appreciated, cartridge 50 is in the form of a modular housing, according to aspects of the invention, at least processor 95 and output device 60 being supported by the modular housing. The modular housing is constructed for insertion into electronic controller 20, such that connector 110 automatically and mechanically aligns with and connects to controller 20 for communication of the connector electrical signal to electronic controller 20 to motivate or reward the patient, as will be described further herein. The modular housing is constructed in the form of a plug-in cartridge. Output device 60 is constructed to be visible to the user of glucose meter cartridge 50 while glucose meter cartridge 50 is inserted into electronic controller 20, as referenced earlier.

According to embodiments of the invention, cartridge 50 or system 10 is, or is part of, an apparatus for encouraging patient compliance with medical monitoring or treatment. The apparatus includes medical diagnostic circuitry or other medical circuitry 115, which can optionally include one or all of input device circuitry 90, processor 95, output device circuitry 100, memory 105 and medical circuitry power supply 120, according to aspects of the invention.

The apparatus also includes motivation circuitry 125. Motivation circuitry 125 is for rewarding and/or motivating a patient, is operatively coupled with medical circuitry 115, and is adapted for communication with an external device, e.g. controller 20, for communicating reward and/or motivation information to the patient or other user of the apparatus. Motivation circuitry 125 is powered by external device 20 and not by power supply 120, according to one aspect of the invention. Motivation circuitry 125 and medical circuitry 115 can be, but need not be, formed as a single circuit board.

Medical circuitry 115 and motivation circuitry 125 are operably connected at 127 (and/or 145, to be described with respect to FIG. 3) by e.g. one or more data-transmission traces, lines, circuits, other hard-wired data links, optical communication, wireless communication, or other form of data transmission. Medical circuitry 115, power supply 120, and motivation circuitry 125 are together supported within plug-in cartridge 50, which is adapted to be received by controller 20 or another external device. Controller 20 or other external device is adapted to communicate with medical circuitry 115 and with motivation circuitry 125 to reward or motivate a user of the apparatus. Of course, controller 20 or other external device also can receive other plug-in cartridges for entertaining a user of the apparatus. For example, a handheld video-game controller 20 can be adapted to receive multiple video game or other game cartridges, as well as cartridge 50. Additionally, cartridge 50 can include a USB port or other external communication port or connector in addition to connector 110, e.g. for connection to additional or alternative types of controllers 20. Thus, according to one embodiment, cartridge 50 can be plugged into a GAME BOY type product, but also can be connected via e.g. a cable to a different brand or type of controller 20. Wireless communications ports or devices for that purpose also are contemplated, according to embodiments of the invention. Thus, dual methods of communication of e.g. medically related data to multiple types of entertainment or other platforms are achieved. The USB port or other communications feature also can be used to download entertainment data, reward data or other information into e.g. motivation circuitry 125 or other feature of cartridge 50.

Embodiments of cartridge 50 also include second processor or support electronics 130 supported by the cartridge housing for communicating motivational or reward information with controller 20. Embodiments of cartridge 50 also include memory 135, adapted to store motivational software to motivate the user of cartridge 50 or system 10 to conduct one or medical tests or otherwise use e.g. glucose meter cartridge 50 or other medical device. Memory 135 is adapted to communicate and/or translate or convert data related to the motivational software to electronic controller 20 via connector 110. Memory 135 also can be adapted to store a video-game or other application and to communicate such application to controller 20 via connector 110. Processor 130 and/or memory 135 optionally are considered portions of motivation circuitry 125.

Figure 3:
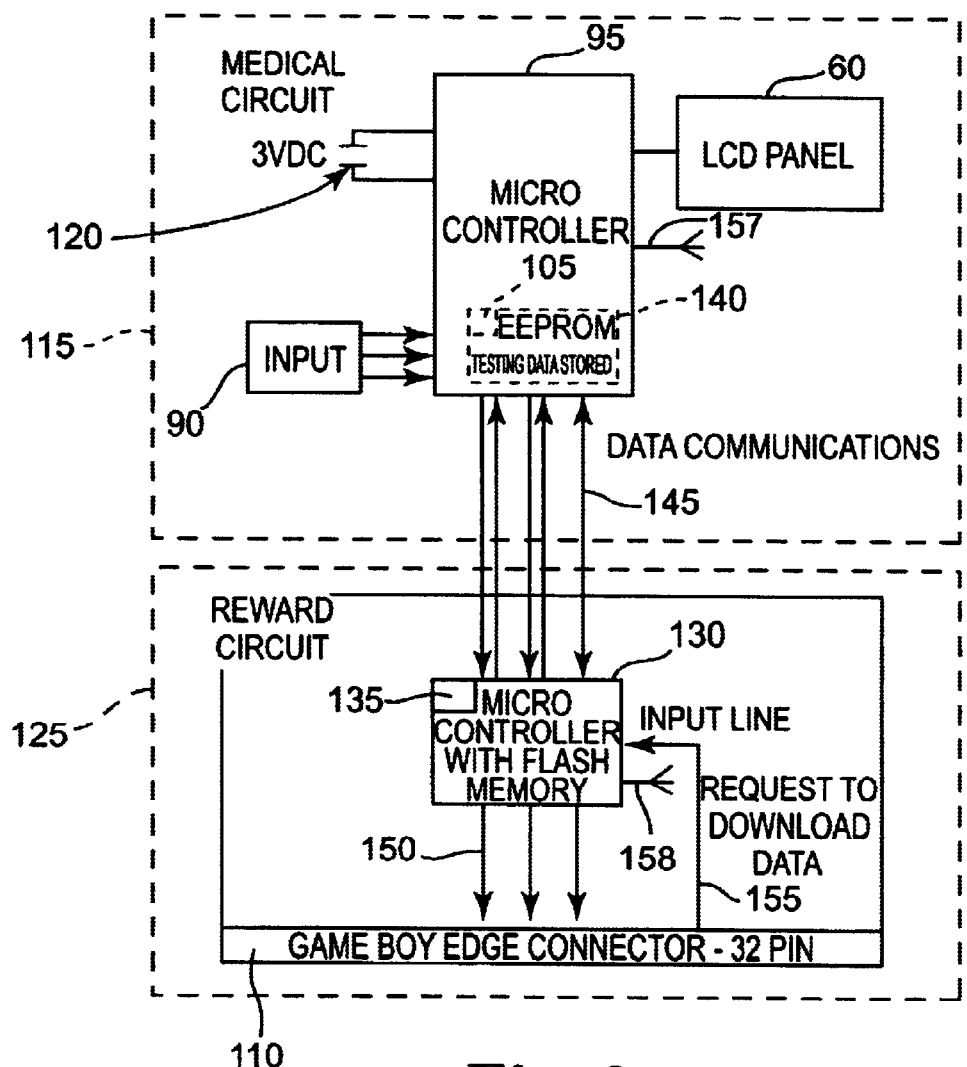
FIG. 3 is a schematic illustration of cartridge circuitry according to an embodiment of the invention.

FIG. 3 illustrates medical diagnostic circuitry or other medical circuitry 115 and motivation circuitry 125 in more detail and in generally schematic form, according to an embodiment of the invention. Medical circuitry 115 includes power source 120, for example a 3VDC battery or other source. Processor 95 includes or can be in the form of a microcontroller with EEPROM 140 and/or flash memory, which can be part of or in addition to memory 105, for e.g. storing testing data, testing data lookup tables or other correlation features, software, or the like. Firmware according to an aspect of the invention is e.g. in the form of a combination of EEPROM 140 with software or data recorded on it. ROMs, PROMs EPROMs, and other storage/memory devices or other devices, in addition to or instead of EEPROM 140, are also contemplated for use. Reward firmware thus is provided in association with motivational circuitry 125, according to embodiments of the invention.

As referenced earlier, input device or input device circuitry 90 can include test-strip insertion slot 75, one or more EKG or EEG sensors, or other devices, operatively coupled with processor 95. Input device or circuitry 90 additionally or alternatively can include an optical sensor operatively coupled with processor 95. Output device 60, in the form of e.g. an LCD panel or other suitable output device, also is operatively coupled with processor 95. Medical circuitry 115 is operatively coupled with motivation circuitry 125 by data communication link(s) 145, referenced previously at 127 in FIG. 2. Motivation circuitry 125 includes second processor and/or electronics 130, according to one aspect, which can include a microcontroller with flash memory, as illustrated. Connector 110 can be e.g. a GAME BOY product 32-pin edge connector. Connector 110 is operatively coupled with second processor 130 by data communication link(s) 150 or other suitable data communication device or system, e.g. of the same type as data communication link(s) 145. Also illustrated in FIG. 3 is input line 155, extending from connector 110 to processor 130. A request to download data can be communicated e.g. from controller 20 or other device via connector 110 and input line 155. Processor 130 receives the request on line 155 and, either alone, or in connection with first processor 95, conveys the requested data along data transmission link 150 to the controller or other external device 20 via connector 110.

Either medical circuitry 115, reward circuitry 125, or both, can include optional antennas 157, 158 or other wired/wireless transmission devices for remote communication. According to one example, new or modified reward or entertainment information can be communicated to cartridge 50 using e.g. BLUETOOTH wireless technology from e.g. a NINTENDO GAMECUBE or other device or location. Connection to a cellular or other wireless communication network is contemplated as well. SMS (short messaging service) or other text messages, graphical messages, and/or voice or other audio messages, can be communicated directly to cartridge 50 via one or more antennas 157, 158 for communication to the user via e.g. display 60. Such communication can provide direct encouragement or motivation, from or as initiated by a doctor, school nurse or other nurse, parent, or other interested person or entity, to encourage or motivate the user to maintain blood glucose values or other medical parameters within certain levels, and/or to maintain a certain testing frequency or regimen, for example. Such communication also can occur via e.g. display 30 of controller 20 or other portion of controller 20. Additionally, encouragement or other messages can be communicated via e.g. display 60 of cartridge 50 without the use of antennas 157, 158 or other external message-directive input; such messages can be pre-programmed within e.g. memory 105 of cartridge 50. Antennas 157 or 158, for example, also can be used to communicate a reply message from the patient via cartridge 50 (and/or controller 20) to the doctor, nurse or other person/entity. Alarm variables or settings, as described herein, also can be communicated via antennas 157 and/or 158.

Embodiments of the invention provide physical separation between medical diagnostic circuitry or other medical circuitry 115 and reward-based or motivation circuitry 125. Medical circuitry 115 maintains its own power supply, while motivation circuitry 125 is powered by controller 20. According to one embodiment, the only physical connection between the two circuits is that of a hardwired interface connection, e.g. at 145, whereby motivation circuitry 125 extracts medical testing data from a specific memory location, e.g. memory 105, within medical circuitry 115. The interface according to one embodiment includes a fail-safe design, so that no sudden power surge or other anomaly is able to adversely affect medical circuitry 115. A dual-diode protection circuit is one example of such a fail-safe design.

Figure 4:
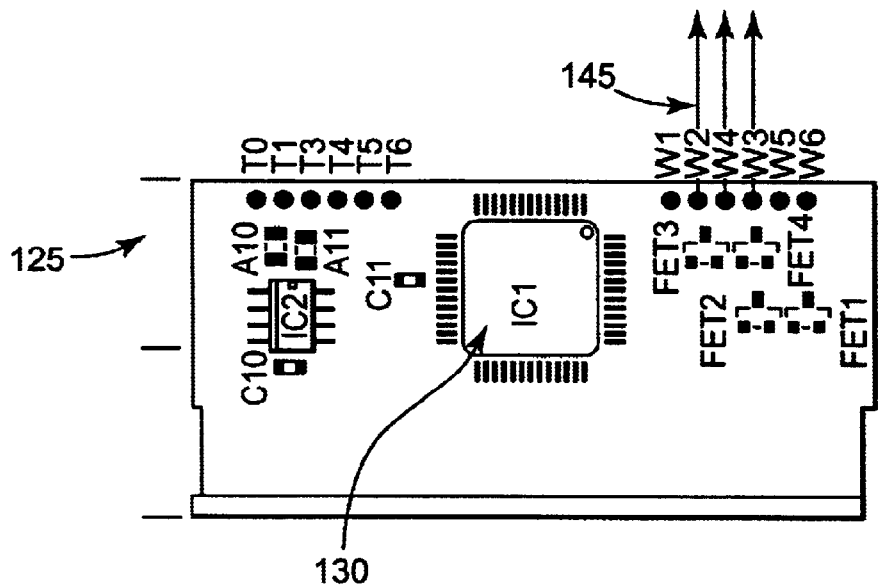
FIG. 4 is a front-side view hardware diagram, according to an embodiment of the invention.
Figure 5:
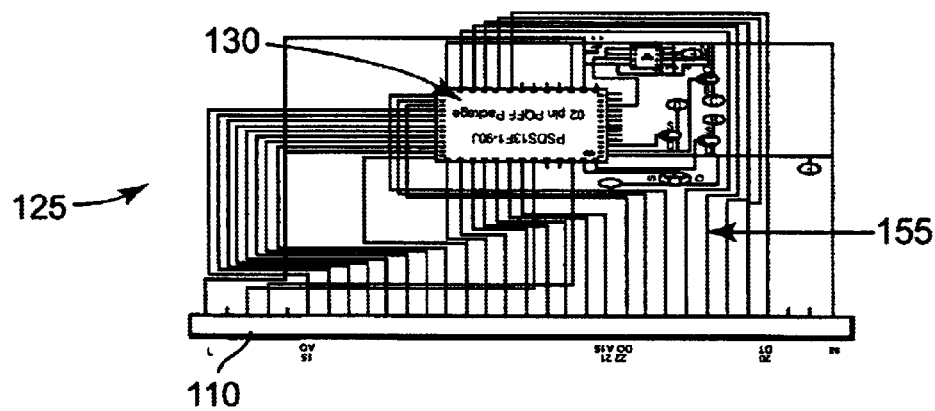
FIG. 5 is a back-side view diagram of the FIG. 4 hardware.

FIGS. 4–5 show the front side and back side, respectively, of one suitable hardware representation of motivation circuitry 125. Microcontroller 130 is operatively coupled to medical circuitry 115 via data communication link(s) 145, and to controller 20 or other external device via line 155, as shown. Embodiments of the invention include features that allow controller 20 or other external device 20, or a remotely located medical professional or other person or entity, to input alarm variables that will be used to alert the patient, and/or to include alarm enunciation via audio and/or visual outputs of controller 20 as to an appropriate time to perform a medical test, when a medical test is overdue, etc. Actual testing time and preset alarm times can be stored by e.g. memory 105 or other memory/storage device. According to embodiments of the invention, audio, visual and/or textual features of cartridge 50 and/or controller 20 can be used to communicate alarm conditions, for example preprogrammed or downloaded alarm conditions, to the patient. For example, in the case where a child or other patient or user has inserted cartridge 50 into a GAME BOY controller or other controller 20 and has passed a deadline or other time for conducting a blood glucose test, then either display 30 of controller 20, or display 60 of cartridge 50, or both, can be activated to flash red as a reminder that a test should be conducted. An audio indication also or alternatively can be provided. Points, ammunition, game levels or other aspects of a pre-existing software game associated with controller 20 can be taken away or denied access, until the test is conducted or other condition that initiated the alarm, e.g. an unacceptable blood glucose level, is satisfied or resolved. As another example, according to cellular telephone embodiments described later in this application, a cellular service or other entity or person can send an SMS or other text message to the cellular phone, and/or generate a special ring or other audio or visual indication, alerting the user that an alarm condition exists and should be remedied or resolved.

According to embodiments of the invention, medical circuitry 115 is or is part of a medical testing device. Motivation circuitry 125 is or is part of a reward-based incentive device operatively coupled with the medical testing device. System 10 correlates how well a patient follows a testing regimen or achieves a certain medical test result using the medical testing device with a reward level provided to the patient by the reward-based incentive device. The correlating function uses the medical test results as a determinant for progression within, regression within, completion of, or elimination from motivational stimuli provided by the reward-based incentive device. The motivational stimuli include a reward code, e.g. a randomized reward code, and/or a video game, according to one embodiment. The means for correlating also can use historical test results as the determinant. Security features also can be provided, such security features including a security device selected from the group consisting of a user-specific access code, and identification code, a password, a DNA sampling device, a fingerprint reader, a retinal scanner, etc. Such security devices are intended to prevent or minimize tampering with user identification, medical test data, or other parameters associated with system 10, to help ensure patient confidentiality, and to provide other advantages.

Figure 8:
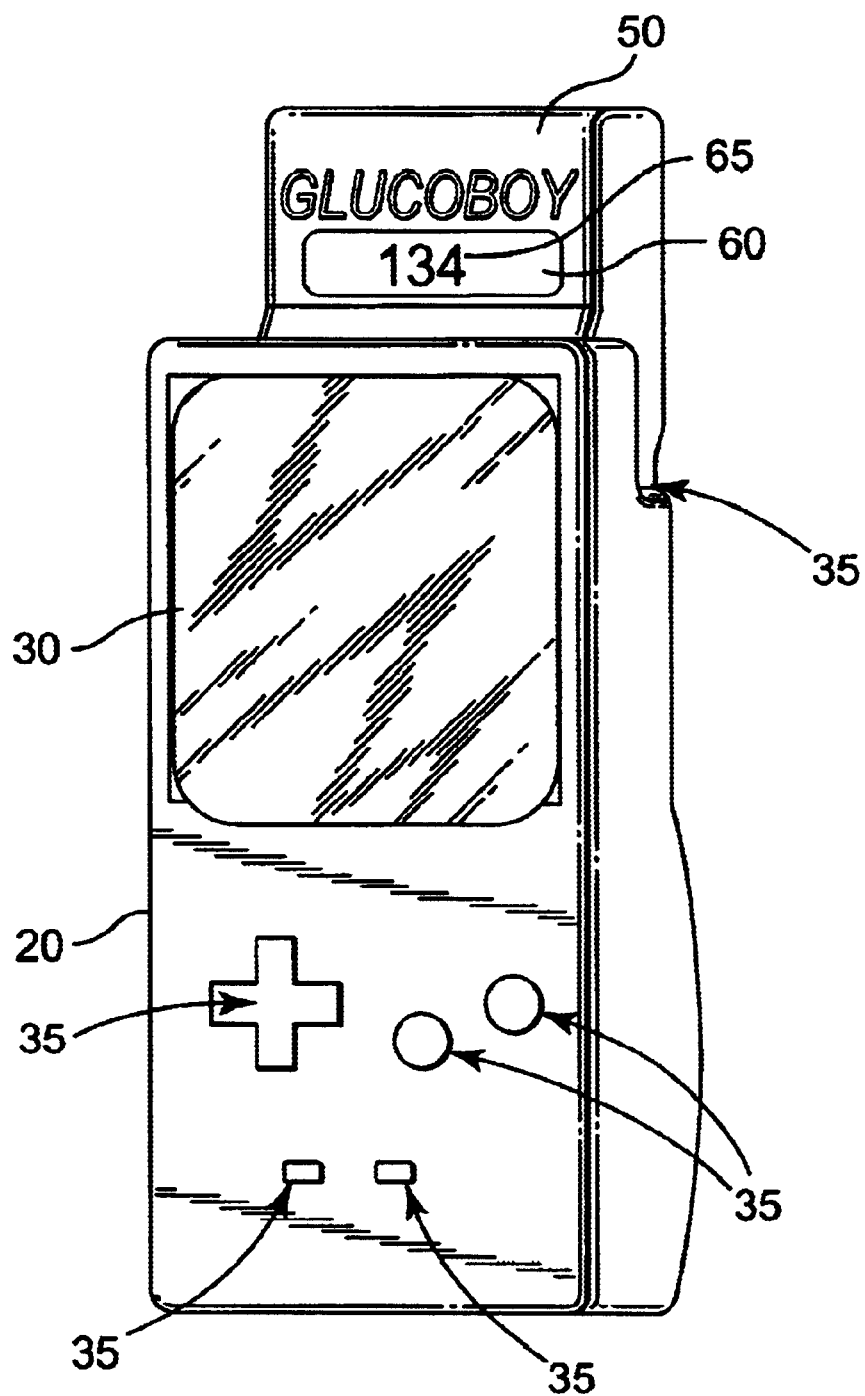
FIG. 8 is a front view of a controller and cartridge together, according to an embodiment of the invention.

FIGS. 6–9 show additional embodiments according to the invention. Video-game controller 20 is adapted to receive game cartridges and includes display 30, in a manner previously described. Medical cartridge 50, for example a medical diagnostic cartridge, is constructed for receipt by video-game controller 20, medical cartridge 50 including display 60, separate from display 30, for displaying medical information to a patient. Controller 20 is adapted to receive medical data from medical cartridge 50 and to display additional information based on the medical data to the patient on first display 30. FIG. 8 shows cartridge 50 inserted into controller 20. Display 30 of GAME BOY controller 20 is used only to display reward codes, games, prizes and other information or incentives that are not directly medically related. Any combination of control keys, buttons or other input devices of controller 20 are used to retrieve reward codes, as will be described, and otherwise interact with controller 20.

Figure 9:
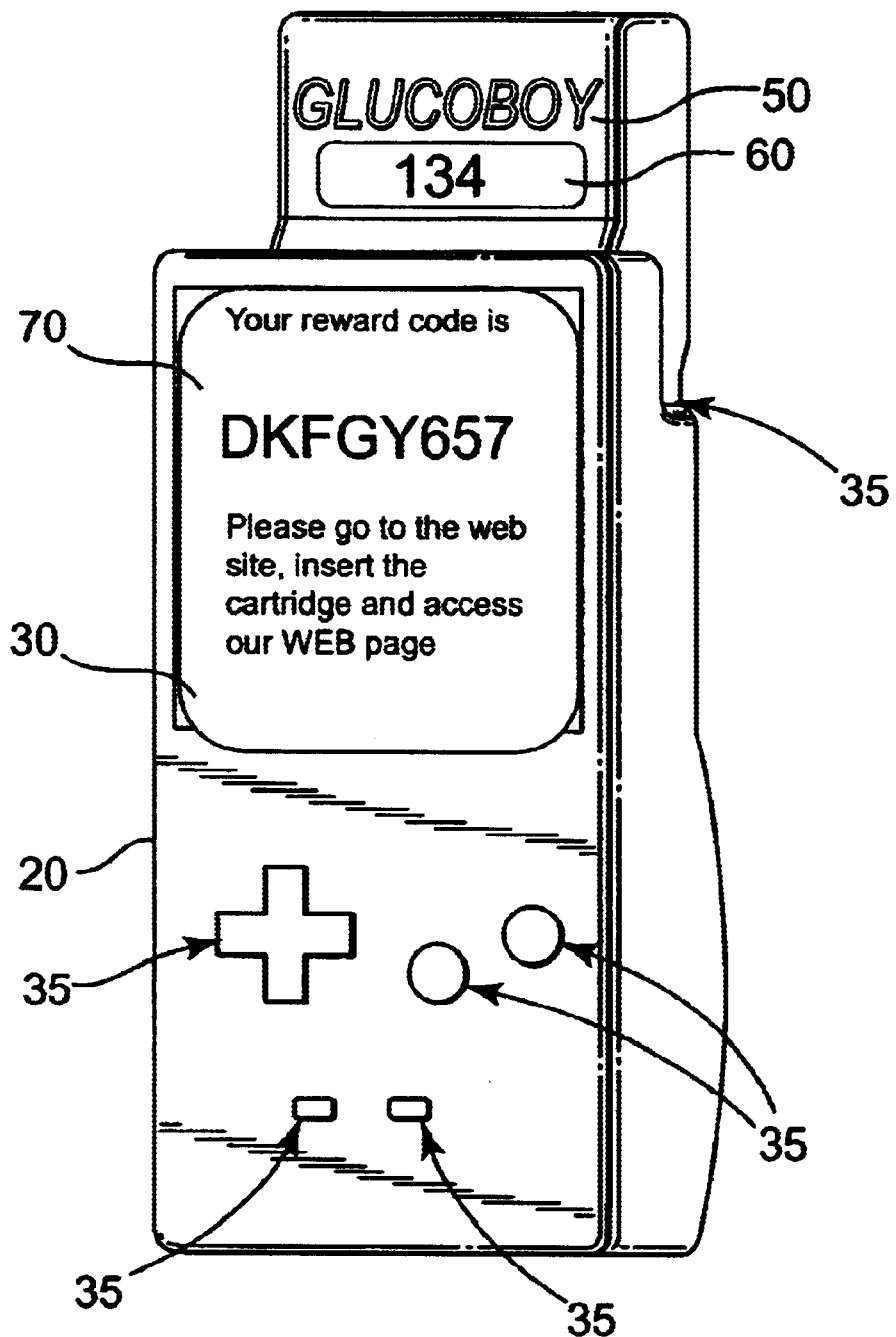
FIG. 9 is a front view of a controller and cartridge together, according to an embodiment of the invention.

FIG. 9 shows one specific example of information 70 shown on display 30. Information 70 includes a reward code. Reward code generation and display to the patient or other user of system 10 is accomplished by randomly generating and displaying a set of characters upon comparison of medical test results by or via cartridge 50 with a predefined reward look-up table that is resident within e.g. the flash memory or other memory 135. Information 70 also can include instructions to access a particular web site for further instruction, reward processing, or other incentive or motivation. Thus, the reward information is chosen to motivate a patient to perform a medical diagnostic procedure, according to one embodiment, and additional information 70 includes a random reward code. Other aspects of the reward code feature of information 70 are described elsewhere herein.

According to one aspect of the invention, controller 20 itself accesses the Internet or other communication network for uploading and/or downloading medical data. Medical data is transferred from cartridge 50 to controller 20, according to one embodiment, and transmitted wirelessly to the communication network. Alternatively, cartridge 50 itself can include wireless communication capabilities for that purpose.

Figure 10:
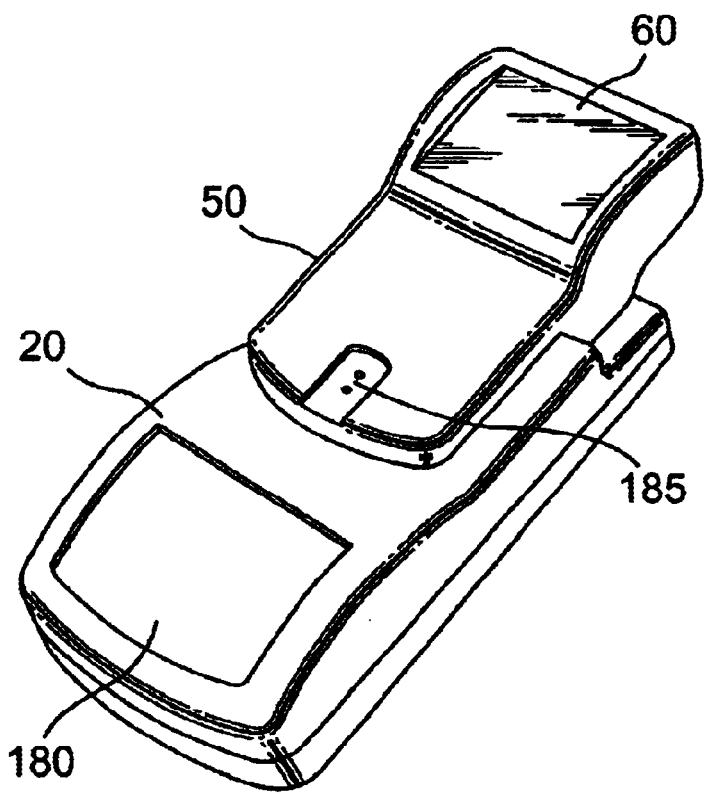
FIG. 10 is a rear view of a controller and cartridge together, according to an embodiment of the invention.
Figure 11:
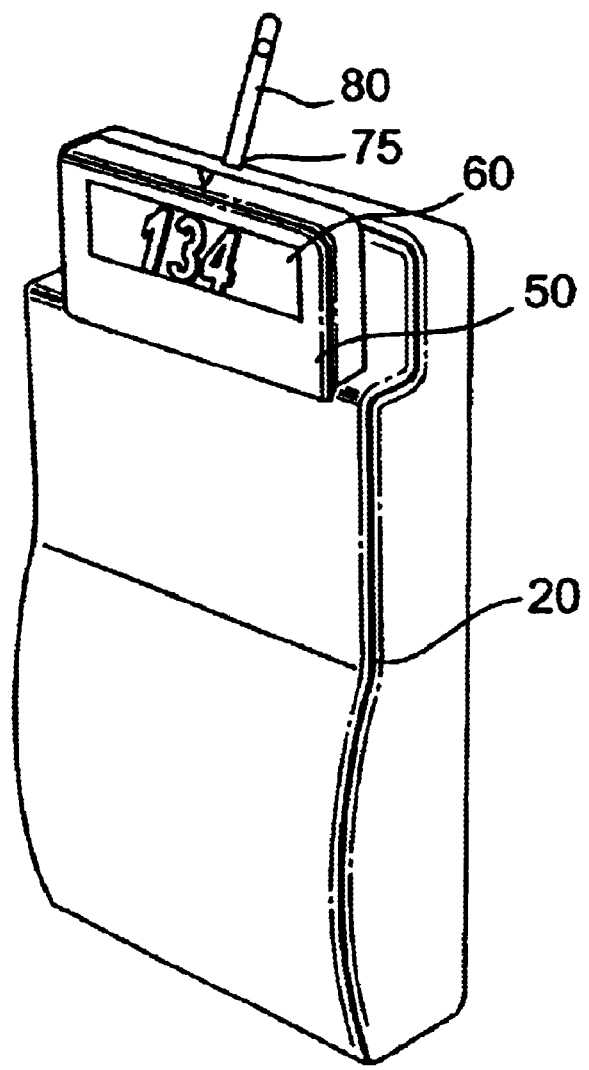
FIG. 11 is a perspective view of a controller and cartridge together, according to an embodiment of the invention.
Figure 12:
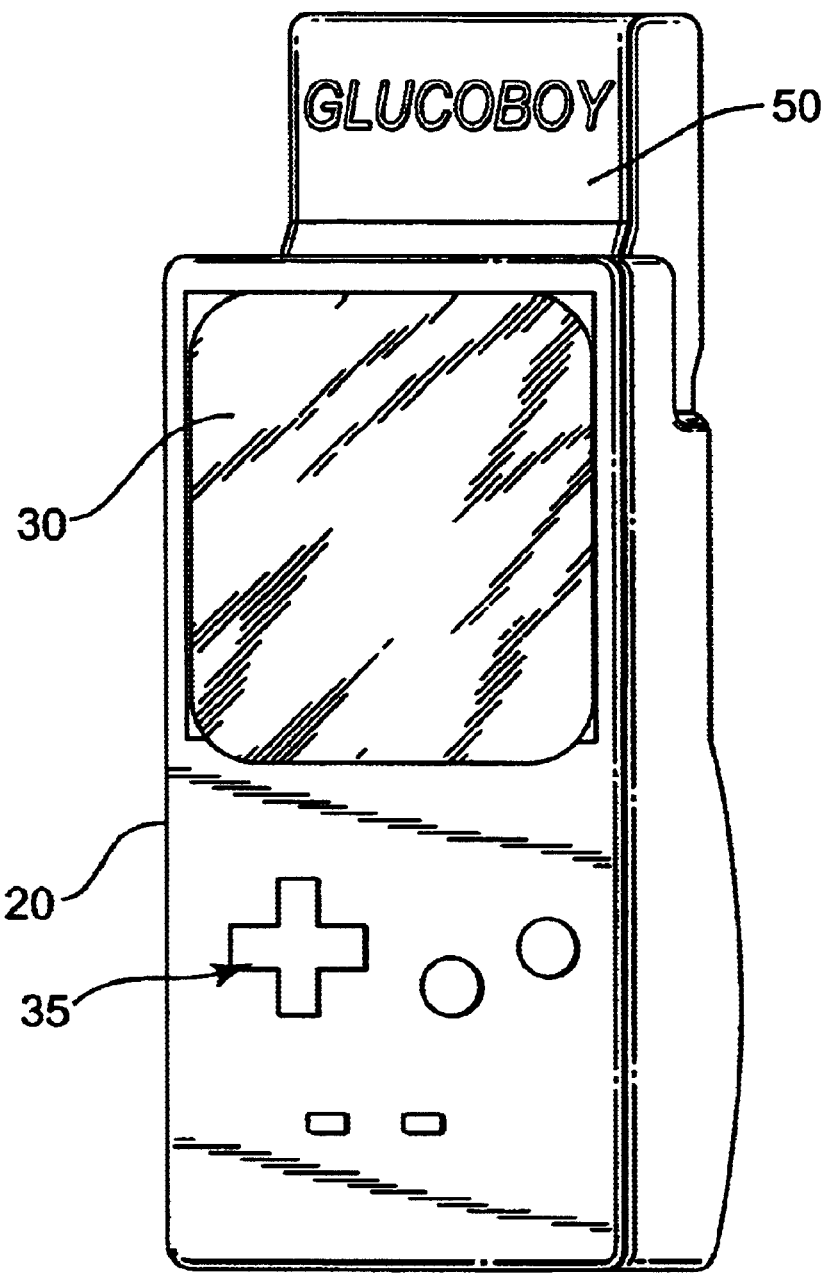
FIG. 12 is a front view of a controller and cartridge together, according to an embodiment of the invention.

FIGS. 10–12 show additional embodiments of controller 20 and cartridge 50. In FIG. 10, controller 20 receives cartridge 50 having a rear-facing display 60 instead of or in addition to the forward-facing display 60 illustrated in e.g. FIGS. 8–9. Controller 20 also can include a rear-facing display 180, instead of or in addition to forward-facing display 30. Also visible in FIG. 10 is rearward-facing physiological input device 185, which can be one of the input devices previously described. FIG. 11 illustrates an embodiment in which cartridge 50 is inserted into a simplified controller 20. Test strip 80 is shown emerging from slot 75 in cartridge 50. One or more optional control keys can be provided on an opposite side of controller 20 from which cartridge 50 as inserted. FIG. 12 illustrates an embodiment of cartridge 50 without a separate display, and/or without a visible separate display. Cartridge 50 can include other ways of communicating medical information to the patient, or can rely on controller 20 to do so, although relying on controller 20 to function as a medical device may have certain regulatory disadvantages, as referenced earlier.

Figure 13:
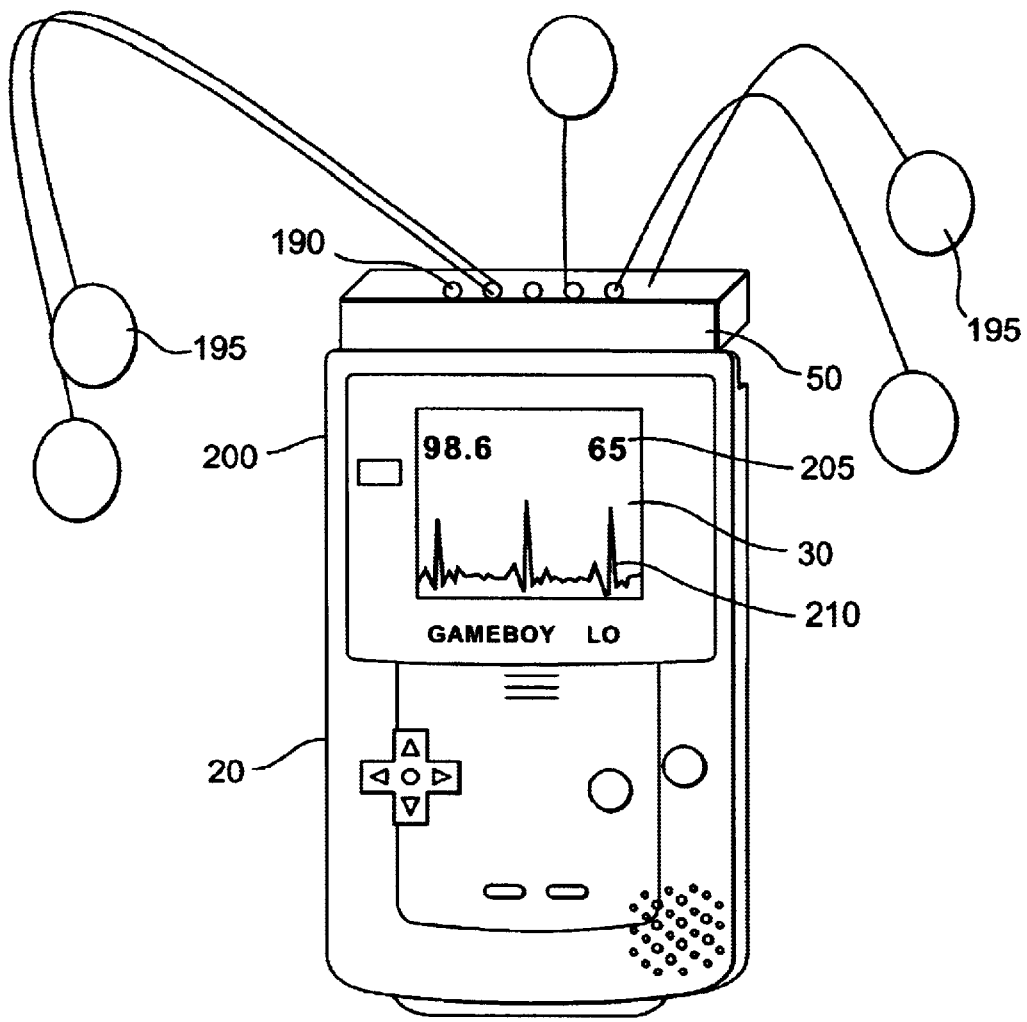
FIG. 13 is a perspective, partially schematic view of a controller and cartridge together, according to an embodiment of the invention.
Figure 14:
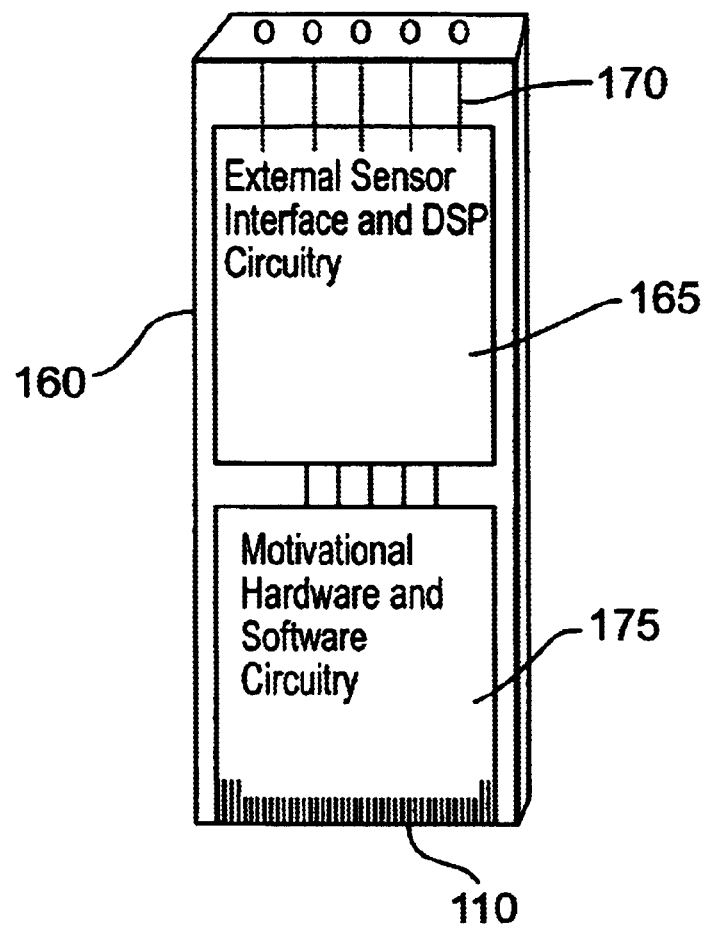
FIG. 14 is a schematic illustration of cartridge circuitry, according to an embodiment of the invention.
Figure 15:
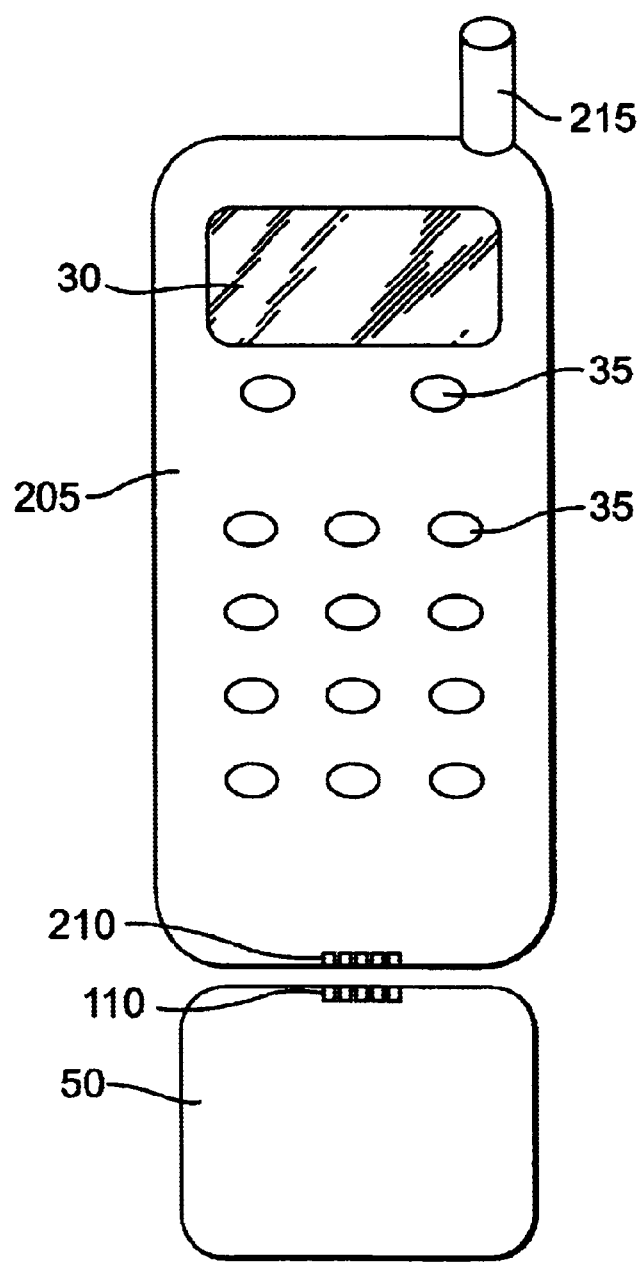
FIG. 15 is a front view of a cellular telephone and cartridge, according to an embodiment of the invention.

An entertainment-type embodiment of the invention is shown in FIGS. 13–14. A high-tech medical kit includes controller 20, insertable gaming cartridge 50 that contains external or discrete sensor input insertion points 190, different types of sensors 195 operatively coupled with insertion points 190, and digital signal processing hardware and software, to be described, housed within or in association with cartridge 50. Cartridge 50 receives different information from sensors 195, which are e.g. pressure, airflow, heart rate, EKG, moisture, temperature, glucose and/or other sensors such as those described elsewhere herein. A unique code embedded in each sensor 195 signals the associated central processor of cartridge 50 as to which sensor is being activated. Appropriate software then enables associated processing functions.

FIG. 14 shows plug-in cartridge 50 for use with the FIG. 13 system. Cartridge 50 includes connector 110 for alignment with and connection to controller 20. Cartridge 50 includes external sensor interface and digital signal processing circuitry as part of its medical or entertainment-related circuitry 115, operably coupled via links 198 to external sensor inputs 190. External sensor inputs 190 can connect to an external glucose meter, for example, or to any of a number of the external medical sensing devices referenced earlier. Motivational hardware and software circuitry 125 is also provided.

Game cartridge 50 according to embodiments of the invention increases interactive learning about different parts of the anatomy, either human or animal. According to one embodiment, motivation circuitry 125, described above, includes appropriate software for communication with controller 20. Using the example of a temperature sensor, for example, a person playing "doctor" obtains temperature readout 200 from a "patient" on display 30. Heart rate 202 and EKG trace 204 are also displayed according to this embodiment. Display 30 is configurable to show one or more inputs from sensors 195 in a desired orientation. Appropriate software allows an operator to understand fundamentals contributing to the patient's temperature, for example. After a current game or learning session is completed, an associated medical examination or quiz allows the doctor/player to be promoted from game level to game level, for example from candy striper to LPN.

FIGS. 15–18 illustrate embodiments of cartridge 50 usable with a controller that is in the form of a cellular telephone 205 or a other wireless communication device. Connector 110 of cartridge 50 optionally can be modified or replaced with a different type of connector (still represented herein as 110, to simplify the disclosure) to insert into or otherwise physically connect with cellular phone data port 210 or other connector. Of course, other types of controllers according to embodiments of the invention, e.g. a personal digital assistant, PALM PILOT product, etc., can be used with a similar or other appropriate data port 210 and/or an appropriate modified cartridge 50, if needed. Cellular telephone 205 or other device preferably includes antenna 215, which can either be an external antenna as illustrated, an internal antenna, or a combination of both antenna types. Other types of controllers 20 also can include an antenna or other device for wireless or other communication. According to one embodiment, cartridge 50 is an adapter module containing e.g. ECG/EKG or other glucose data conversion software, or other medical software, and interactive/motivational software. Cartridge 50 also can be connected to telephone 205 or other controller 20 via an appropriate adaptive mechanism, e.g. an adapter cable, connector or the like.

Figure 16:
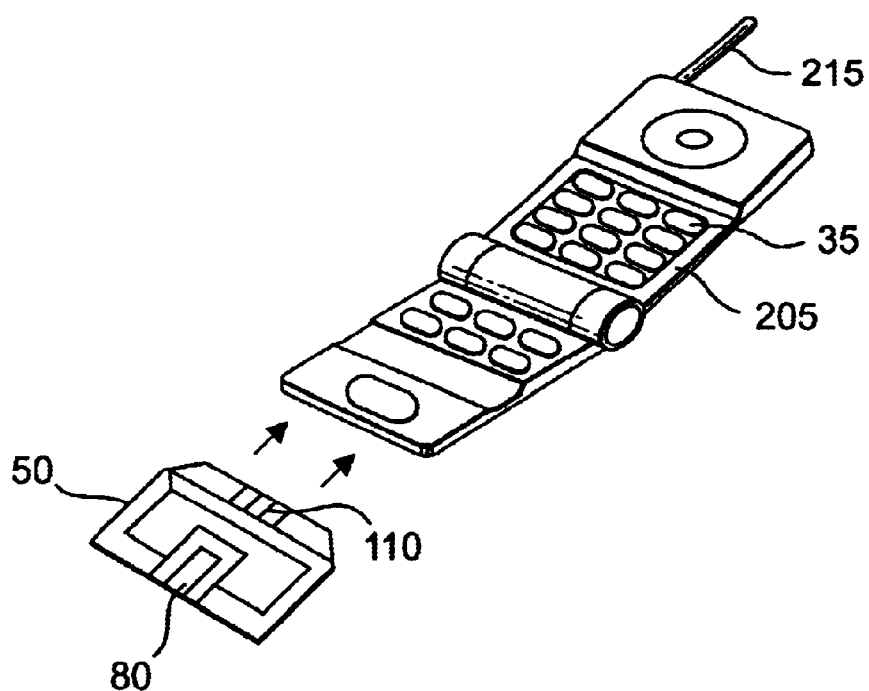
FIG. 16 is a perspective view of a cartridge and a cellular telephone, according to an embodiment of the invention.

FIG. 16 illustrates cartridge 50 for receiving test strip 80 and for connection via connector 110 to cellular telephone 205, which in this case is in the form of a flip-type telephone.

Figure 17:
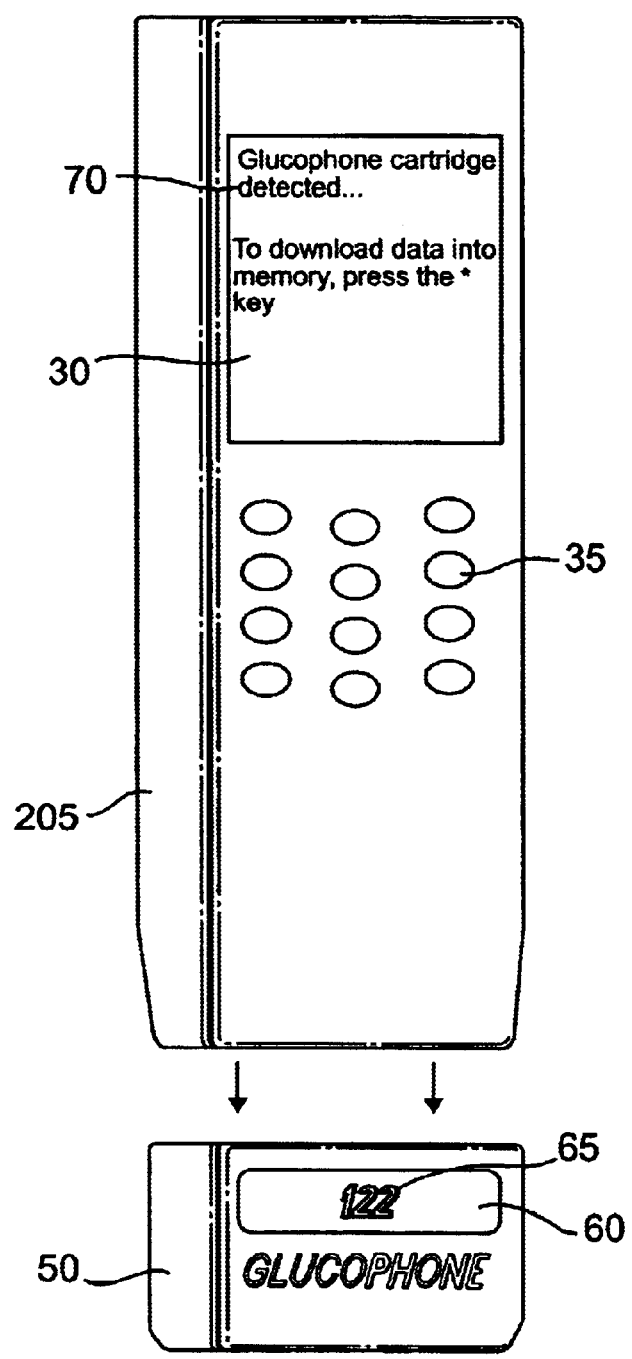
FIGS. 17–18 are front views of a cartridge and cellular telephone, according to an embodiment of the invention.
Figure 18:
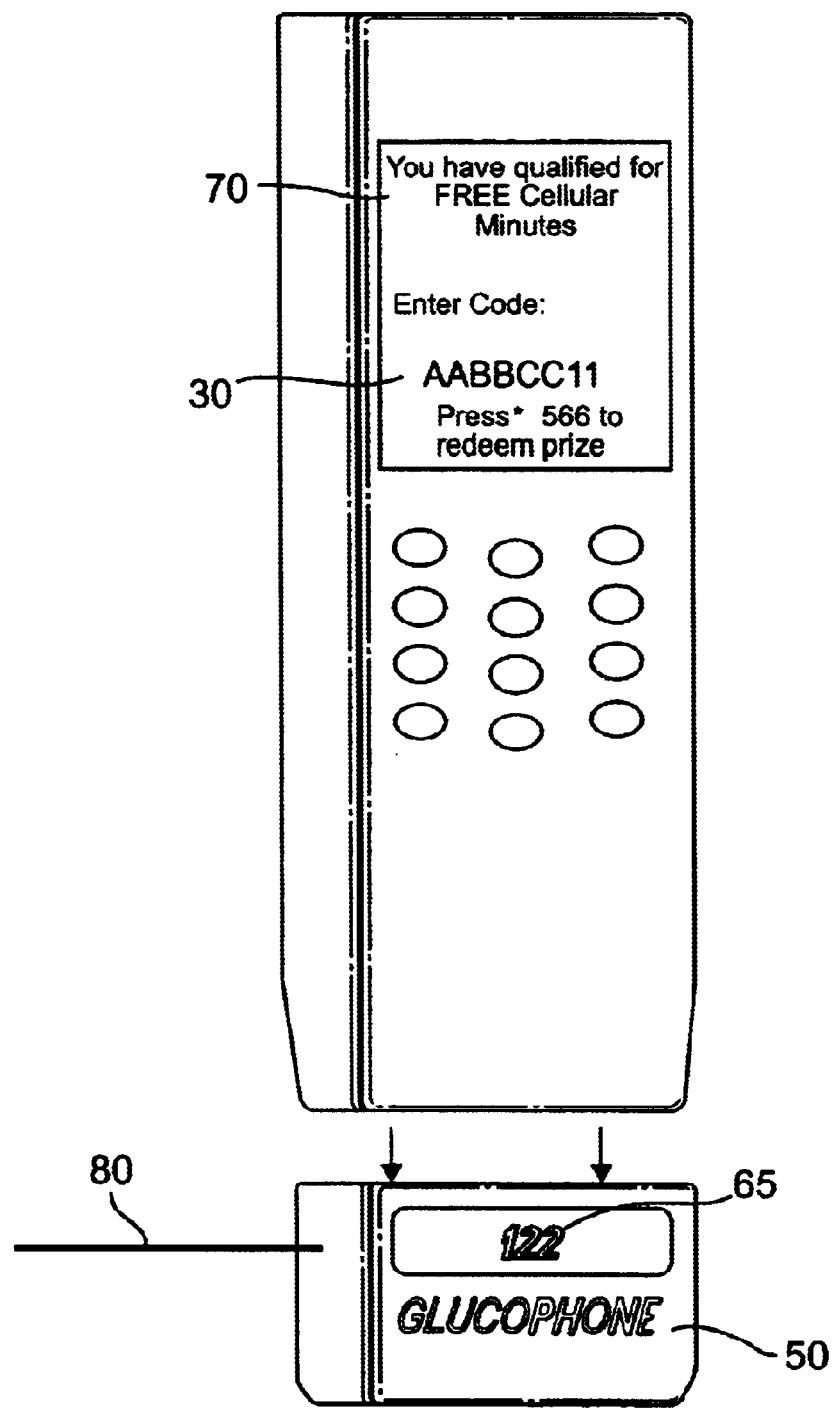

FIGS. 17–18 show cartridge 50 in association with cellular telephone 205. Test strip 80, according to one embodiment, is inserted into cartridge 50 for display of medical information 65 on display 60, for example in the form of a blood glucose reading. Display 30 of telephone 205 provides additional information, for example that cartridge 50 has been detected, instructions to download data into memory by pressing a control key 35, a reward indication, for example that free cellular minutes have been won based on favorable medical information 65 or based on the fact that a test or a certain series of tests have been conducted, a random reward code, and/or instructions for prize redemption.

Embodiments of the invention using cellular telephone or other wireless communication are especially advantageous, because cartridge 50 captures glucose data and stores it in a resident memory, described earlier. The patient or other user then can retrieve glucose data or other medical information 65 by pushing one or more control keys 35 on the keypad of cellular telephone 205. This action downloads the data or other information from cartridge 50 into a special memory location within telephone 205, for example. At this point, the user directs the transmission of the data or information, via pre-existing cellular telephone or other wireless or wired networks, directly to a healthcare provider, independent data warehouse, or other remote location. Healthcare providers and others thus can receive more data more quickly and accurately, to determine a proper treatment regimen and/or determine whether a prescribed treatment regimen is being followed. Reply communications to the patient or other user also are contemplated via the cellular network or other network, for example e-mail messages, SMS messages, voice messages or the like from the health care provider, other qualified individual, or other person, entity or location. This dual communication capability provides and promotes interactivity and direct feedback regarding the glucose or other data being transmitted.

The commercial revenue potential for e.g. a cellular telephone embodiment of the invention is enormous. If a telephone service provider charges even a minimal amount for each data transmission for even a small percentage of the U.S. diabetic market, for example, the annual revenue potential quickly exceeds multiple millions of dollars.

According to cellular telephone embodiments and other embodiments, reward code delivery is accomplished by randomly generating and displaying a set of characters, by comparing medical test results with a predefined reward look-up table that is resident in the flash memory of cartridge 50, for example. The look-up table contains broad areas of discrimination so that the randomized code encourages and/or rewards the patient or other user to maintain testing frequency and/or adjust or maintain current medical test results or other parameters. According to specific embodiments of the invention, the patient or other user is not able to make a medical determination or correlation from the actual medical test displayed on display 60 and the reward code that is displayed on display 30 of controller 20 or telephone 205. However, the reward code may be generated in such a manner that a person or entity with appropriate authorization or a proper unlocking "key" can determine medical test data or other medical parameters based on the reward code. Thus, the reward code can be used to encrypt medical testing parameters such as glucose levels, testing frequency or the like, and the reward code deciphered to determine those parameters.

When cartridge 50 is attached to cellular telephone 205, an identifier code sequence occurs between cartridge 50 and telephone 205, whereby telephone 205 recognizes cartridge 50 as a medical device. After this initial code exchange occurs, telephone 205 readies a specific memory location, for reception of medical testing data and prompts the user for action to download the medical data from cartridge 50 to telephone 205. There, the data resides and awaits user direction as to when the data should be transmitted. The download operation does not erase any of the medical data contained within cartridge 50, according to embodiments of the invention. Display 30 of telephone 205 only displays supplemental information 70 as to e.g. the status of the medical testing data download or transmission. More detailed supplemental information 70, e.g. data transmission times, reception of digital incentives from different entities, etc., are contemplated. Such entities potentially include insurance companies, family members, health-care providers, wireless providers, and/or broadband carriers. If a user decides to transmit stored medical test data, the user can manually input e.g. a telephone number, web address or other location identifier, either manually via control keys 35, by voice, or in another way. Once the user's medical data has been sent to the remote location, a remote reward portal or other reward generation facility generates, based on the medical data, an automated message or reward code and returns it to telephone 205 or other controller 20.

Thus, method embodiments of the invention provide a method of blood glucose data or other medical data transmission. The method includes using a glucose-monitoring device or other medical monitoring device in the form of cartridge 50 to generate glucose data or other medical data. Cartridge 50 is connected to cellular telephone 205, and the glucose data or other medical data is transmitted via a pre-existing telephone network to a remote location. A message is transmitted from the remote location to cellular telephone 205 to provide direct feedback regarding the glucose data or other medical data. A fee can be charged for each data transmission, and the message can be any of a variety of messages in any of a variety of forms, including voice and/or text, SMS, etc.

Figure 19:
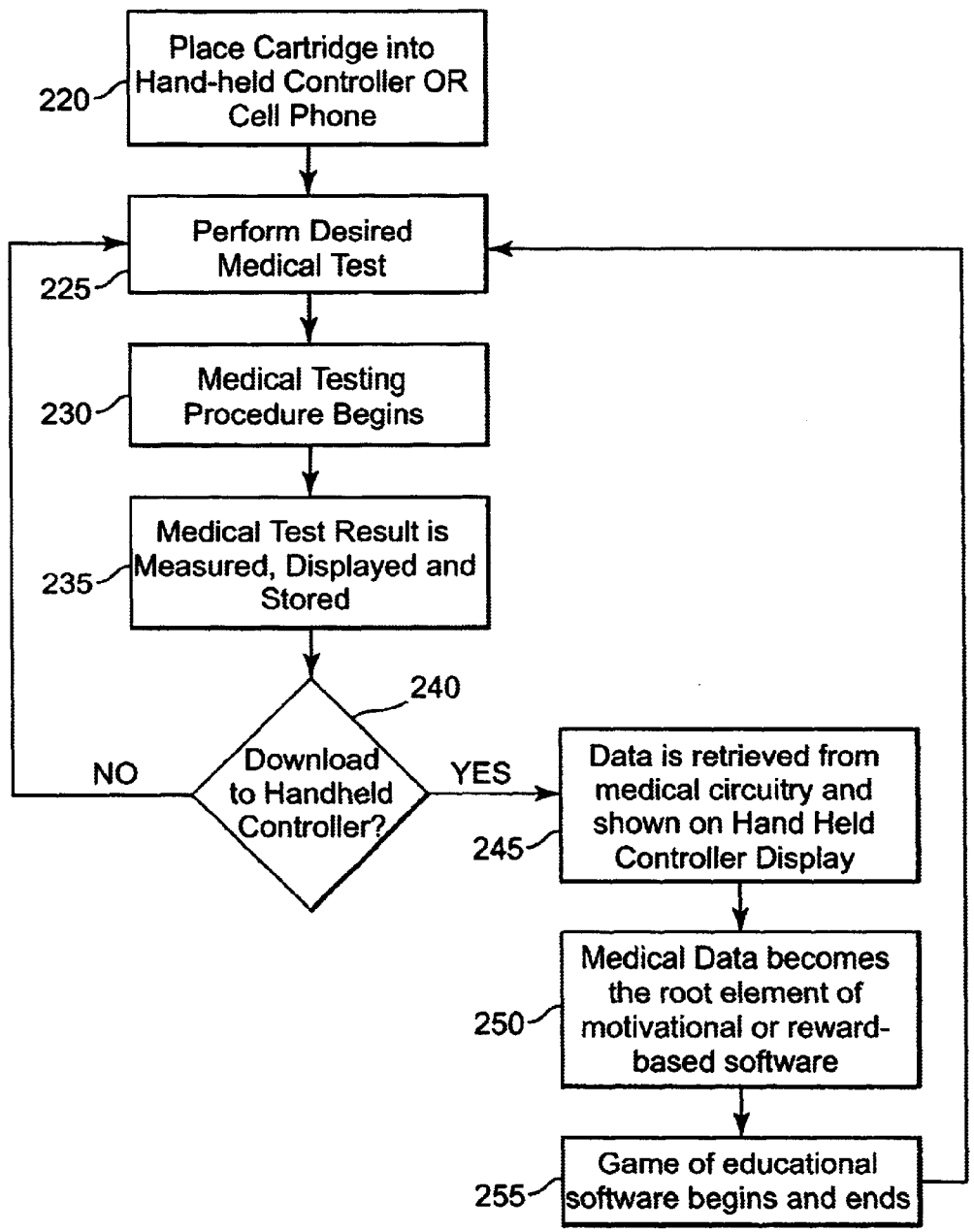
FIGS. 19–26 are flowcharts, according to embodiments of the invention.

According to additional method aspects of the invention, illustrated with respect to e.g. FIG. 19, cartridge 50 is placed into controller 20 at step 220, which controller 20 can include cellular telephone 205. A desired medical test is performed at step 225. Although embodiments of the invention have been described with respect to blood-glucose monitoring, any one or more of a variety of medical tests can be performed, as referenced elsewhere in this application. The medical testing procedure beings at step 230, and a medical test result is measured, displayed and stored at step 235. If an indication occurs at decision step 240 to download data to controller 20, telephone 205 or other device, the method proceeds to step 245. Otherwise, medical testing continues at step 225.

At step 245, data is retrieved from e.g. medical circuitry 115 of cartridge 50 and is shown on display 60 of cartridge 50. Medical data becomes the root element for use by motivation circuitry 125, at step 250. After a game, educational software or other software routine begins and/or ends at step 255, an additional or subsequent medical test is performed at step 225.

Figure 20:
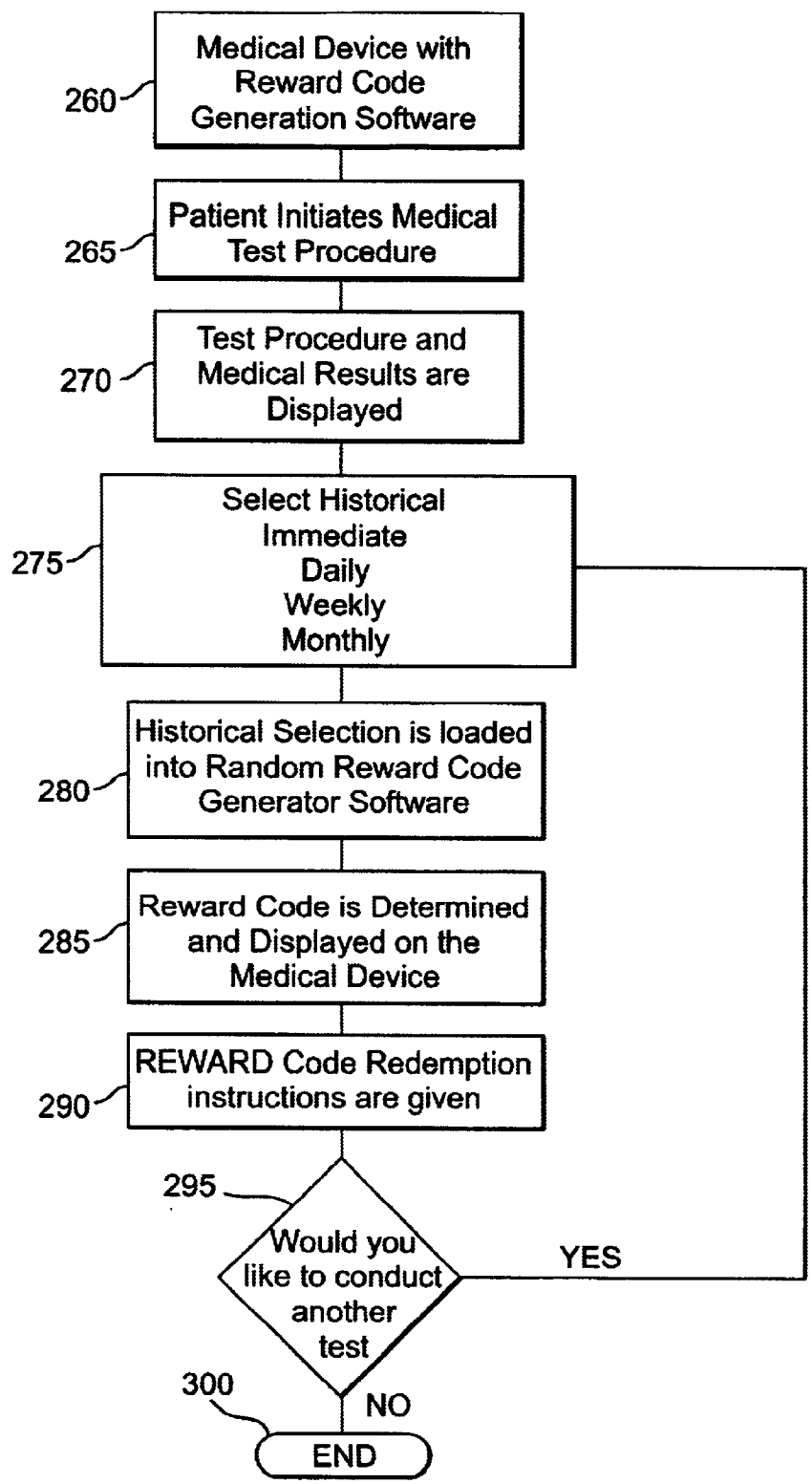

According to the FIG. 20 embodiment, medical device 50 with reward code generation software is activated at step 260. A patient initiates a medical test procedure at step 265, and test procedure and/or medical results are displayed at step 270. The patient or other user then can select historical or other time frame parameters, for example immediate, daily, weekly, monthly or other desired time frame, at step 275. Historical selection criteria is loaded into random reward code generator software at step 280, a reward code is determined and displayed on medical device 50 and/or controller 20 at step 285, and reward code redemption instructions are provided at step 290. The patient is asked whether another test should be conducted at step 295 with the process continuing to ending step 300 or returning to time frame selection step 275, or another desired step in the process, as illustrated.

Figure 21:
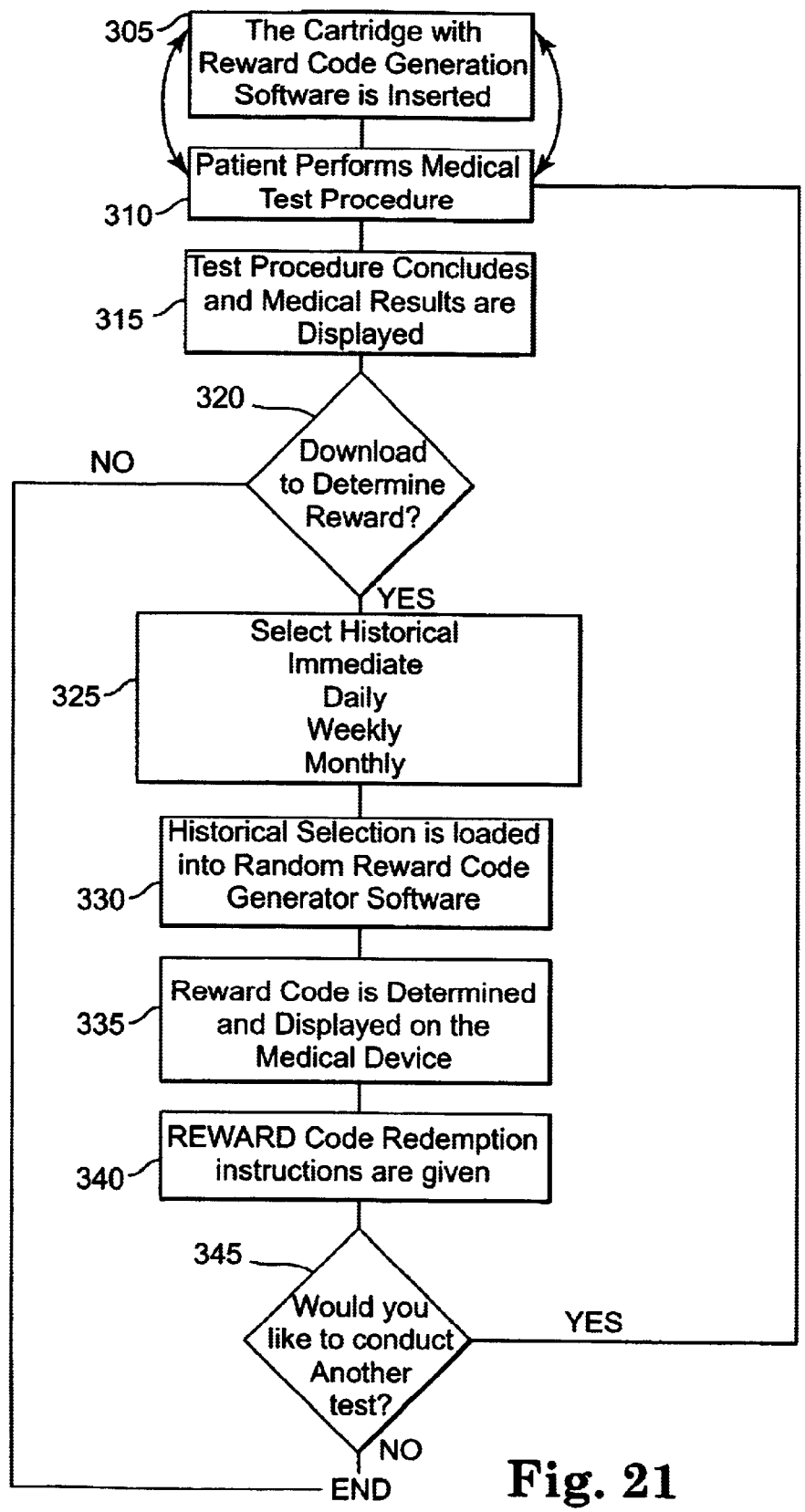

In the case of a reward based on immediate or historical testing data, as shown in FIG. 21, cartridge 50 with reward code generation software is inserted at step 305. The patient performs a medical test procedure at 310, and steps 305, 310 repeat as needed. The test procedure concludes at step 315, and medical results are displayed. If a user chooses at step 320 to download data to determine a possible reward, the patient is directed to select a time frame, at step 325. The historical time frame selection is loaded into the random reward code generator software, at step 330, a reward code is determined and displayed on cartridge 50 and/or controller 20 at step 335, and reward code redemption instructions are given at step 340. If the user wishes to conduct another test at step 345, the process returns to step 310. Otherwise, the process ends.

According to the FIG. 21 embodiment and other embodiments described herein, and as referenced previously, a reward code according to aspects of the invention can be used to encrypt medical testing parameters. At step 330 of FIG. 21, for example, the reward redemption code can be generated in a 12-character format, i.e. as a random or seemingly random 12-character alphanumeric set. But based on pre-specified parameters, lookups or decoding routines, the reward code can be deciphered by e.g. a remote health-care provider or other person or entity to determine e.g. the glucose values for the patient, the frequency with which the patient has tested, and other medical data. A method of encrypting medical data using an entertainment reward code and a method of deciphering the reward code for medical purposes thus are provided, according to aspects of the invention. Because the medical data is not decipherable to the patient, according to this embodiment, the patient cannot use controller 20 as a medical device per se. In fact, according to embodiments of the invention, and as referenced previously, glucose data or readings are not communicated to controller 20, either at all or without appropriate encryption. Medical data can be encrypted according to a random and changing key, before communication to controller 20, so that the patient is precluded from effectively using controller 20 as a medical device and thereby potentially subjecting controller 20 to government regulatory approval requirements, as referenced previously.

Additionally, according to these aspects of the invention, frequency-of-use data can be communicated automatically to a health care provider, medical device company or other entity to report how many glucose test strips or other consumable product is being used, so that additional strips or product can be sent to the patient or other entity without an order being placed in the traditional sense, or a reminder can be sent to e.g. the patient to initiate an order.

Figure 22:
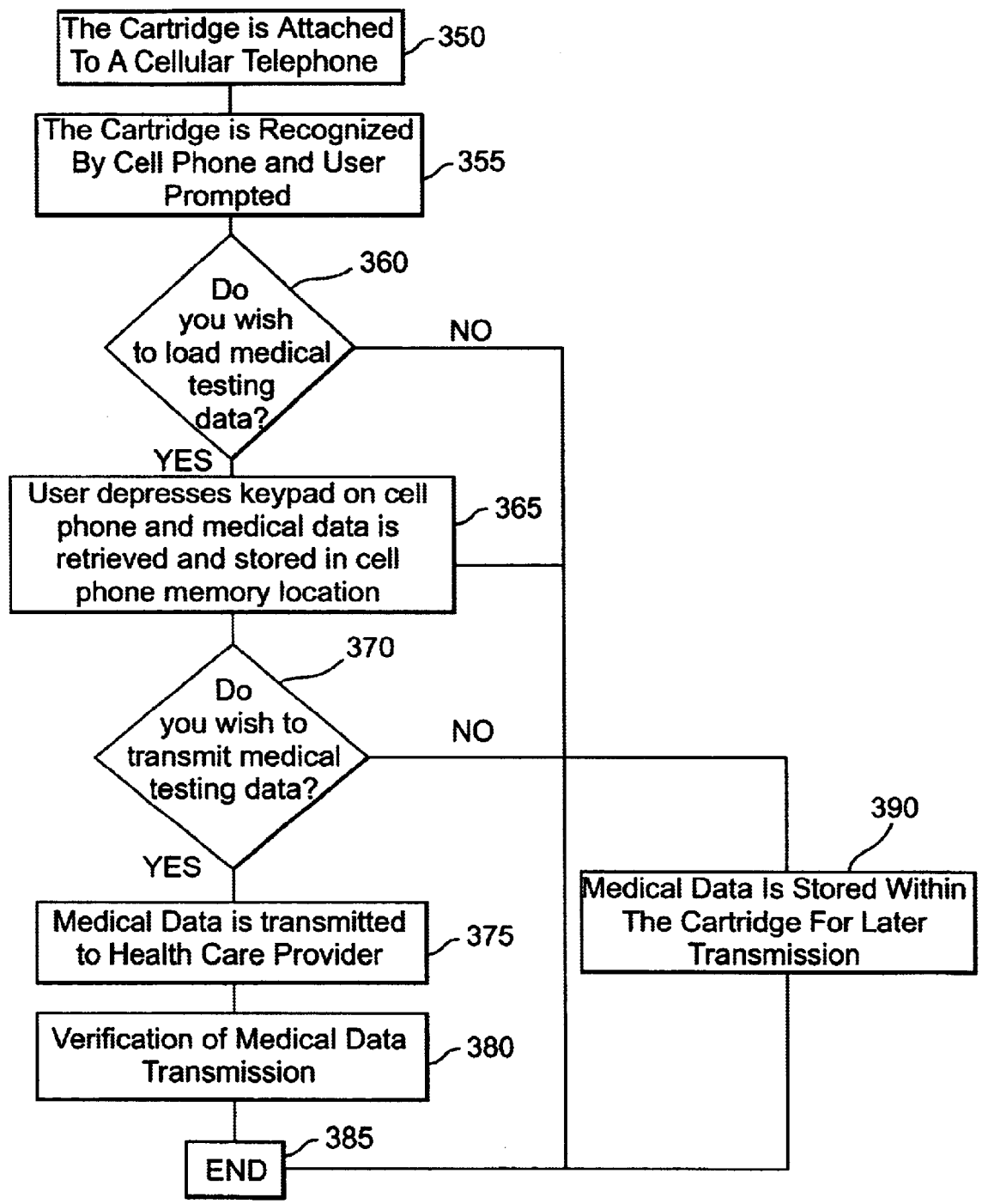

According to the FIG. 22 embodiment, cartridge 50 is attached to cellular telephone 205, or other controller, at step 350. Cartridge 50 is recognized by telephone 205 or other controller 20 and the patient or other user is then prompted, at step 355. At step 360, the user is asked whether the user wishes to load medical testing data. If yes, the user depresses one or more control keys 35 of a keypad, at step 365, and medical data is retrieved and stored in a memory location of e.g. cellular telephone 205. If medical testing data transmission is requested at step 370, medical data is transmitted to a health care provider, qualified person, or other remote person, entity or location, at step 375. Medical data transmission is verified at step 380, and this portion of the process then ends, at step 385. If the user does not wish to immediately transmit medical testing data at step 370, medical data is stored within cartridge 50 for later transmission, at step 390.

Figure 23:
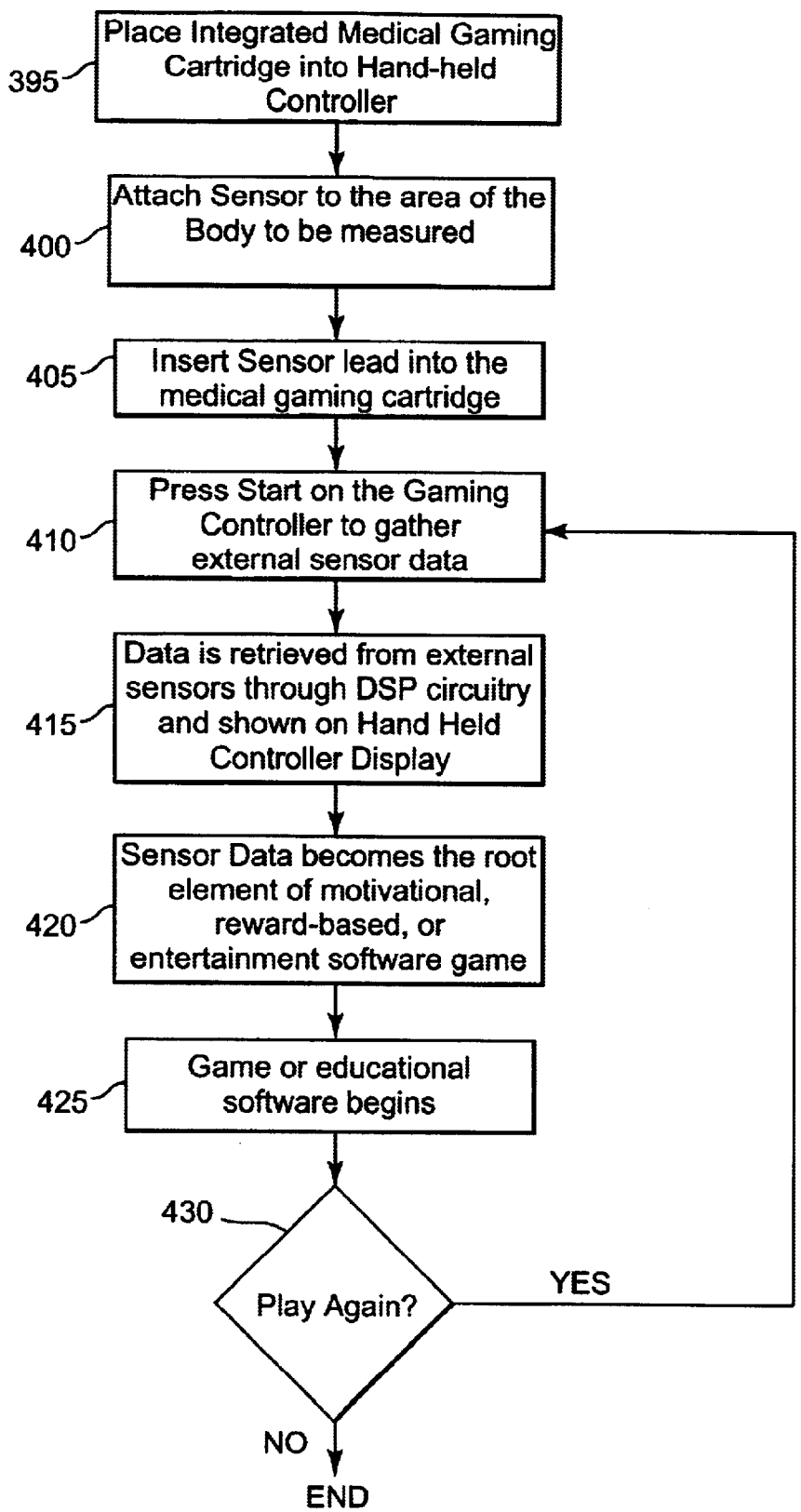

According to a medical entertainment process for sensor acquisition and game progression illustrated in FIG. 23, cartridge 50 is placed into controller 20, at step 395. One or more sensors, for example sensors 195, are attached to an area of the body to be measured, or otherwise provided with appropriate physiological input, at step 400. Sensor leads are inserted into cartridge 50, for example at insertion points 190, at step 405. One or more control keys 35, for example a "start" key, is depressed on gaming or other controller 20 to gather external sensor data, at step 410. At step 415, data is retrieved from sensors 195 through digital signal processing circuitry and is shown on display 30 of controller 20. At step 420, sensor data becomes the root element of motivational, reward-based, or entertainment-oriented software, for example a software game. The game or other application begins at step 425, and, once ended, the user can decide at step 430 whether to play again or not.

Figure 24:
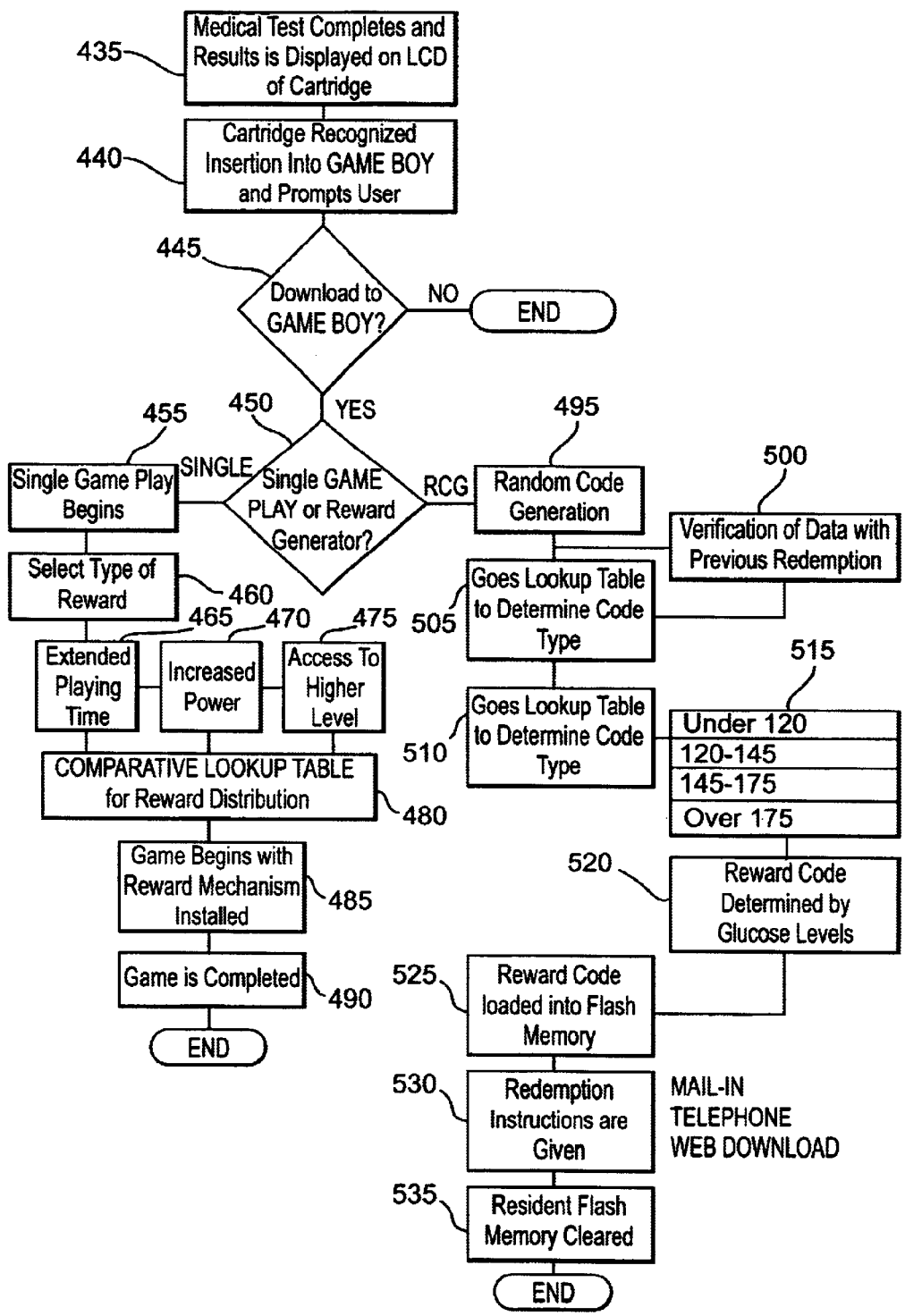

FIG. 24 illustrates a game reward and random code generation embodiment within the same cartridge program. At step 435, a medical test is completed and results are displayed on e.g. display 60 of cartridge 50. At step 440, cartridge 50 is inserted into controller 20, recognized, and initiates a user prompt. At step 445, the user is asked whether it is desired to download medical data or other data from cartridge 50 to controller 20. If yes, the user is prompted at step 450 as to whether single game play or reward generation is desired. If single game play is selected, single game play begins at step 455. Then, a type of reward is selected at step 460, for example extended playing time 465, increased power 470, access to a higher level 475, or other reward. Other examples of rewards include extra points, extra ammunition or other asset, promotion to a different level of play, and the like. Providing reward information can include providing these and other digital incentives for use with either pre-existing software games or other entertainment media that are not necessarily medically oriented, or with medically oriented games or media.

According to specific embodiments, off-the-shelf game or other software is provided with special levels of play or other incentives, access to or use of which is provided only in connection with medically related determinants. For example, access to a special or advanced game level can be provided if a user maintains a certain testing schedule or maintains one or more chosen medical parameters, e.g. blood glucose, within certain thresholds. The special levels or other incentives can be accessed only in connection with medical devices or results according to embodiments of the invention. Additionally, or alternatively, the pre-existing software game, stored within e.g. memory 105 of cartridge 50, also can be changed, e.g., by downloading a new software game or other application either directly to cartridge 50 or to cartridge 50 via controller 20. According to embodiments of the invention, a greater reward value is provided when results of medical tests are maintained within certain thresholds or are close to an optimum level. Greater reward value also can be provided if medical tests are conducted according to a predetermined or other schedule or with a predetermined frequency. Comparative look-up table access for reward distribution occurs at step 480. A game or other application begins at step 485, and the game or other application is completed at step 490.

If reward generation is selected at step 450, random code generation occurs at step 495. Verification of data with a previous redemption can occur at step 500. A look-up table is accessed at step 505, to determine a random code, a type of random code, or other information. If an additional code, code type or other information is desired, a second look-up table or other random code generator can be accessed at optional step 510. Glucose levels are matched to a reward type at steps 515, 520. At step 525, a determined reward code is loaded into flash memory or other memory. Redemption instructions are given at step 530. The redemption instructions can include mail-in redemption, telephone redemption, coupon generation, and/or web-download redemption, for example. The flash or other memory type is cleared at step 535 to end the process.

Figure 25:
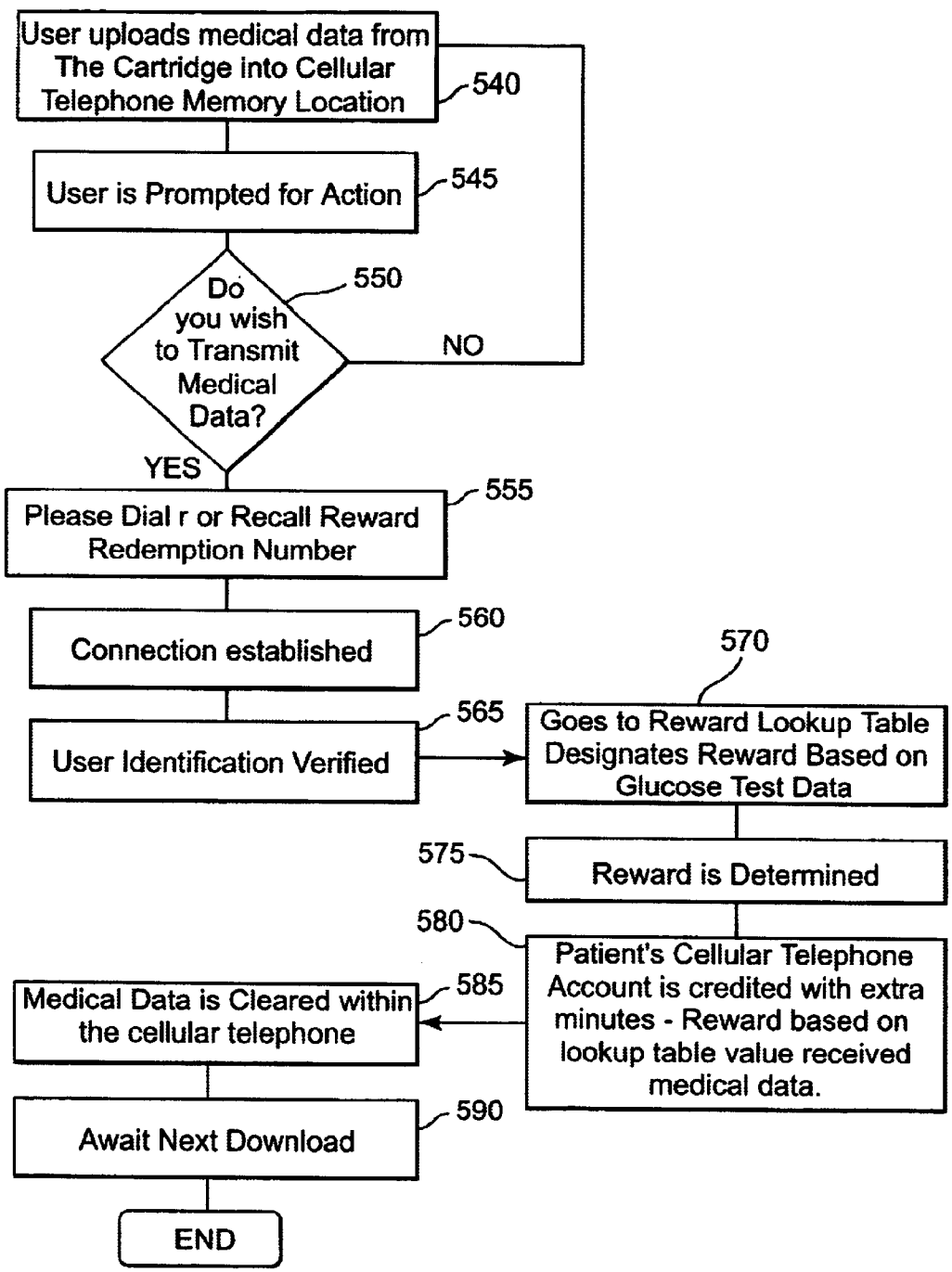

According to the FIG. 25 embodiment, a user uploads medical data at step 540 from cartridge 50 into telephone 205 or other controller 20. At step 545, the user is prompted for action. If medical data transmission is selected at step 550, an instruction is given at step 555 to dial "R" or to recall a reward redemption number, for example. Connection is established at step 560, user identification is verified at step 565, a reward look-up table is accessed at step 570 and a reward is designated based on e.g. glucose test data or other medical data. A reward is determined at step 575, and, at step 580, the patient or other user's cellular telephone account is credited with extra minutes or another reward is provided. The reward is based on a look-up table value based on the medical data. At step 585, the medical data is cleared within telephone 205, controller 20 and/or cartridge 50, if desired. At step 590, the next download is awaited.

Figure 26:
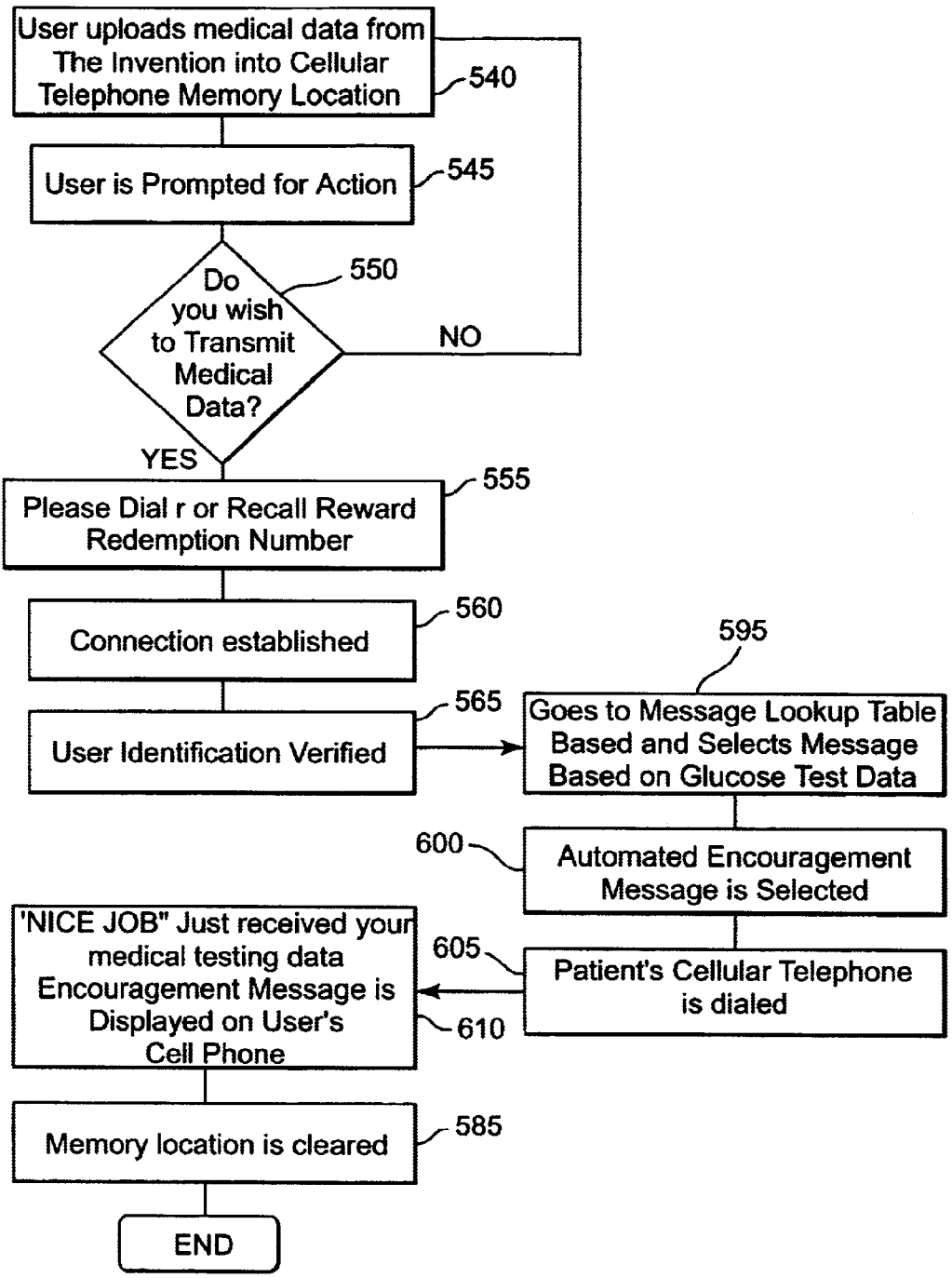

The FIG. 26 embodiment is substantially similar to the FIG. 25 embodiment, except that a message look-up table is accessed at step 595 and a message is selected based on glucose test data or other medical data. An automated encouragement message is selected, at step 600. The message can include video, graphics, text, and/or audio, to name several examples. At step 605, the patient's telephone 205 is dialed. At step 610, as one example, a "nice job" message or other encouragement message is displayed on e.g. display 30 of telephone 205. Previously referenced memory locations are cleared at step 585, and the next download awaited.

Figure 27:
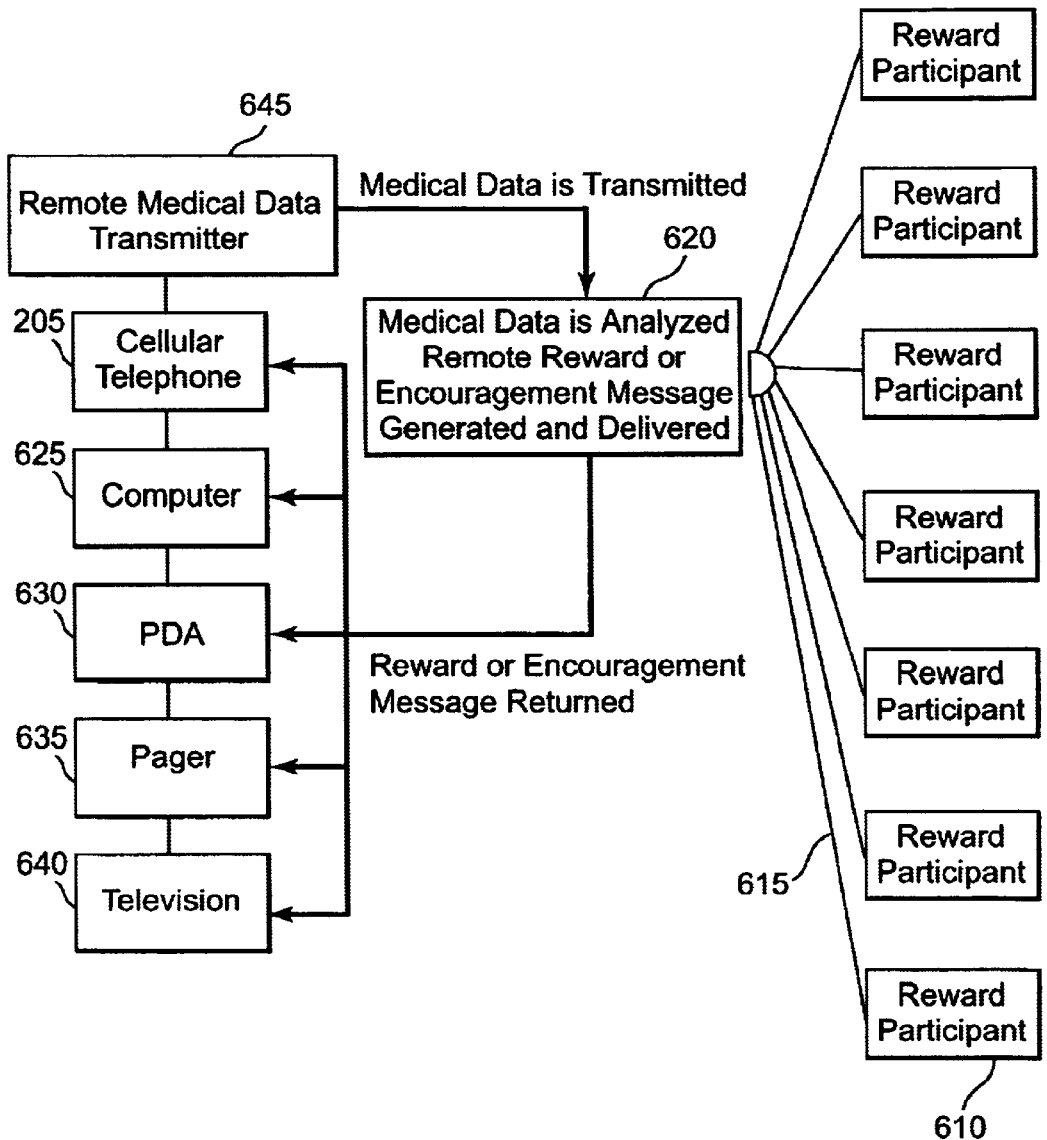
FIG. 27 is an illustration of network communication, according to an embodiment of the invention.

As illustrated in FIG. 27, multiple reward participants, patients, or other users 610 transmit medical data over communications network 615, for example a cellular telephone communications network, the Internet, a conventional telephone network, a radio-frequency network, a television network, a LAN, a WAN, etc. Medical data is analyzed and a remote reward or encouragement message generated and delivered at 620. The reward or encouragement message can be returned to a communication device belonging to one or more reward participants 610 and/or that is remote from reward participants 610. Such communication hardware can include cellular telephone 205, computer 625, personal digital assistant 630, pager 635, and/or television 640, to name several examples of controller 20. The communication hardware devices optionally can be interconnected, and/or connected to remote medical data transmitter 645 for transmission of medical data for analysis at 620. Additionally, with appropriate confidentiality precautions or waivers in place, data or messages based on one reward participant's medical test can be transmitted to one or more other reward participants and used in e.g. tracking software, gaming software, or the like to promote competition or otherwise encourage multiple reward participants to conduct medical tests or maintain medical test results within desired parameters.

Stored data can be transmitted to other computing devices in a wireless or other format. Graphs and/or plots of historical values, of one or more reward participants, can be generated on display 30 of controller 20. Downloading from cartridge 50 or transmission to a remote location can occur by e.g. an integrated motivational software menu selection function, and data transmitted through resident communication ports of controller 20, for example.

Thus, a communications network is used to communicate motivational information to the patient from an external or remote source, the source being selected from the group consisting of a medical service provider, telephone service provider, telephone service carrier, cable provider, Internet service provider, satellite service provider, insurance carrier, and healthcare professional. The network can be used to download to a preset medical testing schedule established by e.g., a healthcare provider. The preset medical testing schedule can be downloaded into a programmable exercise device, a television set top box appliance, a hand-held computer, cellular telephone, or other controller 20. The actual testing time of the medical tests conducted can be compared with the downloaded or otherwise generated preset medical testing schedule. According to user-programmed embodiments, the testing regimen or schedule can be chosen and entered by the patient or other user. The reward information provided to the patient can be reconfigured, based on the patient's age, demographic status, or other factor.

In addition to those described previously, different types of sensors and applications usable according to embodiments of the invention include: (1) photo-electrics (e.g. heart sensing, blood sensing, height sensing), (2) piezo-resistive (e.g. strength measurement, weight measurement, heartbeat detection, lung capacity measurement, (3) pressure (e.g. lung capacity, blood pressure, pressure-based scalpel technique), (4) mass air flow (e.g. lung capacity), (5) fiber optics (e.g. inner ear measurement or viewing), (6) thermocouple (e.g. body or appendage temperature sensing), (7) carbon dioxide sensing (e.g. heart and lung software), (8) oxygen sensing (e.g. heart and lung software), (9) moisture sensing (e.g. sweat analysis, dermatology software), (10) glucose monitoring, as described herein, and/or (11) ultrasonics (e.g. profiling bone structure, height measurement, heartbeat monitoring).

According to more entertainment-oriented embodiments, hardware/software is offered in different versions or at different levels, e.g. an EMT version, army medic version, veterinarian version, emergency room version, etc. Advancement, promotion or progression is provided based on medical testing data, frequency and/or schedule, e.g. promotion through a hierarchical progression of military ranks. Compliance with medical testing or parameters, or other successful management of diabetes or other disease, would earn advancement from e.g. private to sergeant to lieutenant, etc. Telephone modem, e-mail, Internet access, and other communication modes already incorporated in e.g. the GAME BOY product or other off-the-shelf device enable remote teaching/grading from educational facilities or other remote locations. Thus, an effective incentive tool for teachers and students is provided. Other, more detailed versions or contemplated for e.g. personal computers, PlayStations, Nintendo machines and other machines in addition to the GAME BOY type device.

Those of ordinary skill will appreciate that a variety of medical tests can be included or used according to any of the embodiments of the invention referenced herein. For example, in addition testing for blood glucose, medical testing according to the invention can include testing for HbA1c, blood pressure, lipids, cholesterol, peak-flow, oxygen saturation, spirometer data, exercise, heart rate, body fat, prescription adherence, medical laboratory testing, body weight, chemotherapy, temperature, kidney dialysis, neuropathy, and many other tests, testing devices, or the like.

Additional aspects of the invention allow a user to manually or otherwise input additional medical parameters to be monitored or tested, in addition to one or more primary or first-entered medical parameters. For example, many diabetics must be concerned with blood pressure monitoring in addition to blood glucose level monitoring. Blood pressure data can be manually or otherwise entered and used to provide additional digital incentives, e.g. promotion or play levels, in addition to those based on blood glucose or other primary parameter. As an additional example, HbA1c levels typically are determined at a lab or outside testing facility. Embodiments of the invention allow a child or other patient to input their HbA1c level, or even to guess or be quizzed as to what a desirable HbA1c level (or any other medical parameter or level) might be, and those levels or guesses used to provide digital incentives. Thus, embodiments of the invention educate the patient about the importance of long-term diabetes management as well as merely short-term diabetes management, according to one example. Hyperlipidemia or blood cholesterol level data also can be entered and used. Providing reward and/or motivation to appropriately manage e.g. blood glucose, blood pressure and blood cholesterol levels according to aspects of the invention, or at least to promote and improve knowledge of appropriate associated health management skills, can greatly improve patient management of these conditions and greatly reduced the medical, social, financial and other costs due to poor management. Associated reminders to test multiple parameters, e.g. reminders that a time has arrived to monitor blood pressure as well as blood glucose, also can improve patient management skills and/or motivation. Diet, exercise, and other activities, tests or the like also can be encouraged or rewarded, according to the invention.

While the invention has been described and illustrated with respect to particular embodiments, the invention is not to be considered limited to such embodiments. Many modifications and changes will be apparent to those of ordinary skill in the art. Devices other than GAME BOY devices, PDA's, and the other off-the-shelf devices referenced herein are usable according to embodiments of the invention, for example. Other glucose monitoring devices or methods, e.g. those of a more conventional nature, can be used instead of EKG/EEG monitoring devices and methods, in connection with embodiments of the invention. Embodiments of the invention also can be used in connection with e.g. asthma and/or epileptic seizure detection devices and methods. Additionally, although certain features according to the invention may be described with respect to a particular controller, e.g. a cellular telephone, and/or with respect to a particular process, e.g. those described with respect to FIGS. 19–26, it should be noted that equal application of those features to other controllers or other processes/devices is also contemplated. In other words, any feature described with respect to one particular embodiment can be considered to apply equally to the other embodiments. Other variations will be apparent to those of ordinary skill.

What is claimed is:

1. A medical monitoring system comprising:
   a hand held computing device comprising an input device, an operating system, a power supply, and a physical interface connection for loading of different software programs; and
   a module comprising:
   a medical testing device for performing a medical test;
   medical diagnostic circuitry, operably coupled with the medical testing device, for performing medical analysis;
   video game circuitry for motivating or rewarding a user of the system, the medical diagnostic circuitry being adapted to send medical testing results data to the video game circuitry, the video game circuitry being adapted to store medical testing results data for determination of reward data to motivate the user, the video game circuitry further being adapted to receive electrical input from the hand held computing device;

a housing for both the medical diagnostic circuitry and the video game circuitry;

a display on the housing for displaying medical testing results;

an interface that provides a physical connection between the module and the physical interface connection of the hand held computing device to send reward data to the hand held computing device; and a module power supply within the medical diagnostic circuitry;

wherein the module comprises a stand-alone medical testing cartridge adapted for insertion into the hand held computing device.

2. The system of claim 1, wherein the hand held computing device comprises a video-game controller for receiving video-game cartridges.

3. The system of claim 1, wherein the hand held computing device comprises a cellular telephone.

4. The system of claim 1, wherein the band held computing device comprises a wireless communication device.

5. The system of claim 1, wherein the medical testing device comprises a blood-glucose testing device.

6. The system of claim 1, wherein the medical testing device defines an aperture adapted to allow insertion of a medical blood test strip for performing a blood glucose analysis.

7. The system of claim 1, wherein the medical testing results data comprises blood-glucose test data.

8. The system of wherein the medical testing results data is selected from the group consisting of: HbA1c test data, blood-pressure test data, lipids test data, cholesterol test data, peak-flow test data, oxygen-saturation test data, spirometer test data, exercise-based test data, heart-rate test data, body-fat test data, prescription-adherence test data, medical-laboratory test data, body-weight test data, chemotherapy-based test data, temperature-based test data, kidney-dialysis test data, and neuropathy test data.

9. The system of claim 1, wherein the medical testing results data comprises a determinant for progression within, regression within, completion of, or elimination from motivational stimuli provided td the user by the hand held computing device.

10. The system of claim 9, wherein the motivational stimuli comprise a reward code and a video game.

11. The system of claim 1, further comprising an interface between the medical diagnostic circuitry and the video game circuitry, the interface comprising a hardwired interface or a wirelessly coupled interface.

12. The system of claim 1, wherein stored medical testing results data is stored in a specific memory location within the video game circuitry.

13. The system of claim 1, wherein the hand held computing device comprises a display for displaying the reward data or information based on the reward data.

14. The system of claim 1, wherein the display on the housing of the module is adapted to display the reward data or information based on the reward data.

15. The system of claim 1, wherein the medical testing cartridge defines a connection feature for connection to a second computing device independent of the hand held computing device.

16. The system of claim 15, wherein the connection feature comprises a USB port or a wireless communications port.

17. A method of using the system of claim 1, wherein the hand held computing device comprises a cellular telephone, the method comprising:

connecting the module to the cellular telephone;

transmitting the medical testing results data via a re-existing cellular telephone network to a remote location; and transmitting a message from the remote location to the cellular telephone to provide direct feedback regarding the medical testing results data.

18. The method of claim 17, further comprising charging a fee for each medical testing results data transmission.

19. The method of claim 17, wherein the medical testing results data is blood-glucose data and the module is a blood-glucose monitoring device.

20. A method of using the system of claim 1, the method comprising:

generating a reward code based on the medical testing results data, wherein the medical testing results data, or a parameter based on the medical testing results data, is encrypted within the reward code; and using the reward code to motivate the patient to manage a medical condition related to the medical testing results data.

* * * * *